(12) United States Patent
Bonner et al.

(10) Patent No.: US 8,560,064 B2
(45) Date of Patent: *Oct. 15, 2013

(54) EXTRAVASCULAR ARRHYTHMIA INDUCTION

(75) Inventors: Matthew David Bonner, Plymouth, MN (US); Kevin Patrick Kuehn, Shoreview, MN (US); Vladimir Pavlovich Nikolski, Blaine, MN (US); Joseph L. Sullivan, Kirkland, WA (US); William John Havel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1402 days.

This patent is subject to a terminal disclaimer.

(21) Appl. No.: 12/183,517

(22) Filed: Jul. 31, 2008

(65) Prior Publication Data
US 2010/0030290 A1    Feb. 4, 2010

(51) Int. Cl.
*A61N 1/39*    (2006.01)

(52) U.S. Cl.
USPC .................................................. 607/5

(58) Field of Classification Search
USPC ........................................ 607/4–8
See application file for complete search history.

(56) References Cited

U.S. PATENT DOCUMENTS

| | | |
|---|---|---|
| 4,768,512 A | 9/1988 | Imran |
| 5,105,809 A | 4/1992 | Bach, Jr. et al. |
| 5,129,392 A | 7/1992 | Bardy et al. |
| 5,261,400 A | 11/1993 | Bardy |
| 5,292,338 A | 3/1994 | Bardy |
| 5,346,506 A | 9/1994 | Mower et al. |
| 5,653,740 A | 8/1997 | Degroot et al. |
| 5,824,018 A | 10/1998 | Dreher et al. |
| 6,453,197 B1 | 9/2002 | Parry et al. |
| 6,937,896 B1* | 8/2005 | Kroll ................................ 607/9 |
| 7,181,275 B2 | 2/2007 | Havel |
| 7,289,854 B2 | 10/2007 | Bardy et al. |
| 7,319,898 B2 | 1/2008 | Hess |
| 2003/0195569 A1 | 10/2003 | Swerdlow et al. |
| 2004/0106955 A1 | 6/2004 | Swerdlow et al. |

(Continued)

FOREIGN PATENT DOCUMENTS

WO    2004026398 A1    4/2004

OTHER PUBLICATIONS

Sharma et al. "Shock on T Versus Direct Current Voltage for Induction of Ventricular Fibrillation . . . " Pacing Clin. Electrophysiol. 27(1):89-94, Jan. 2004.

(Continued)

*Primary Examiner* — Joseph Dietrich
(74) *Attorney, Agent, or Firm* — Michael C. Soldner

(57) ABSTRACT

A cardiac arrhythmia may be induced by delivering a sequence of pulses to a patient via one or more extravascular electrodes. In one example, one or more pacing pulses may be delivered to a patient via an extravascular electrode and a shock pulse may be delivered to the patient the extravascular electrode. In some examples, the pacing pulses and the shock pulse may be generated with energy from a common energy storage module and without interim charging of the module. For example, the pacing and shock pulses may be generated as the energy storage module dissipates. In another example, a cardiac arrhythmia may be induced in a patient by delivering a burst of pulses to a patient via an extravascular electrode. In some cases, the burst of pulses may be generated with energy from a common energy storage module and without interim charging of the energy storage module.

29 Claims, 14 Drawing Sheets

(56) References Cited

U.S. PATENT DOCUMENTS

| | | |
|---|---|---|
| 2006/0122649 A1 | 6/2006 | Ghanem et al. |
| 2006/0247687 A1 | 11/2006 | Swerdlow et al. |
| 2007/0213774 A1 | 9/2007 | Kameli |
| 2008/0033494 A1 | 2/2008 | Swerdlow |

OTHER PUBLICATIONS

Mazer et al. "Transcutaneous T Wave Shock: A Universal Method for Ventricular Fibrillation Induction" Pacing Clin. Electrophysiol. 20(12 part 1):2930-5, Dec. 1997.

Sanders, Jr. et al. "Ventricular Fibrillation Induction Using Nonsynchronized Low Energy External Shock . . . " Pacing Clin. Electrophysiol. 19(4 part 1):431-6, Apr. 1996.

Hauer et al. "The T-Wave Shock: A New Reliable Method for Induction of Ventricular Fibrillation in ICD Testing" Z Kardiol. 84(4):284-8 Apr. 1995.

Rosenfeld et al. "Ventricular Tachycardia Induction: Comparison of Triple Extrastimuli with an Abrupt Change . . . " Am Heart J. 111(5):868-74 May 1986.

U.S. Appl. No. 11/969,663, filed Jan. 4, 2008 entitled "Apparatus for Noninvasive Induction of Ventricular Fibrillation" by Havel et al.

U.S. Appl. No. 12/183,486, filed Jul. 31, 2008 entitled "Extravascular Arrhythmia Induction" by Bonner et al.

Office Action from U.S. Appl. No. 12/183,486, dated Mar. 7, 2011, 8 pp.

Response to Office Action dated Mar. 7, 2011, from U.S. Appl. No. 12/183,486, filed Jun. 7, 2011, 10 pp.

Response to Office Action dated Apr. 23, 2012 from U.S. Appl. No. 12/183,486, filed Jul. 17, 2012 (14 pages).

Office Action from U.S. Appl. No. 12/183,486 dated Apr. 23, 2012 (8 pages).

* cited by examiner

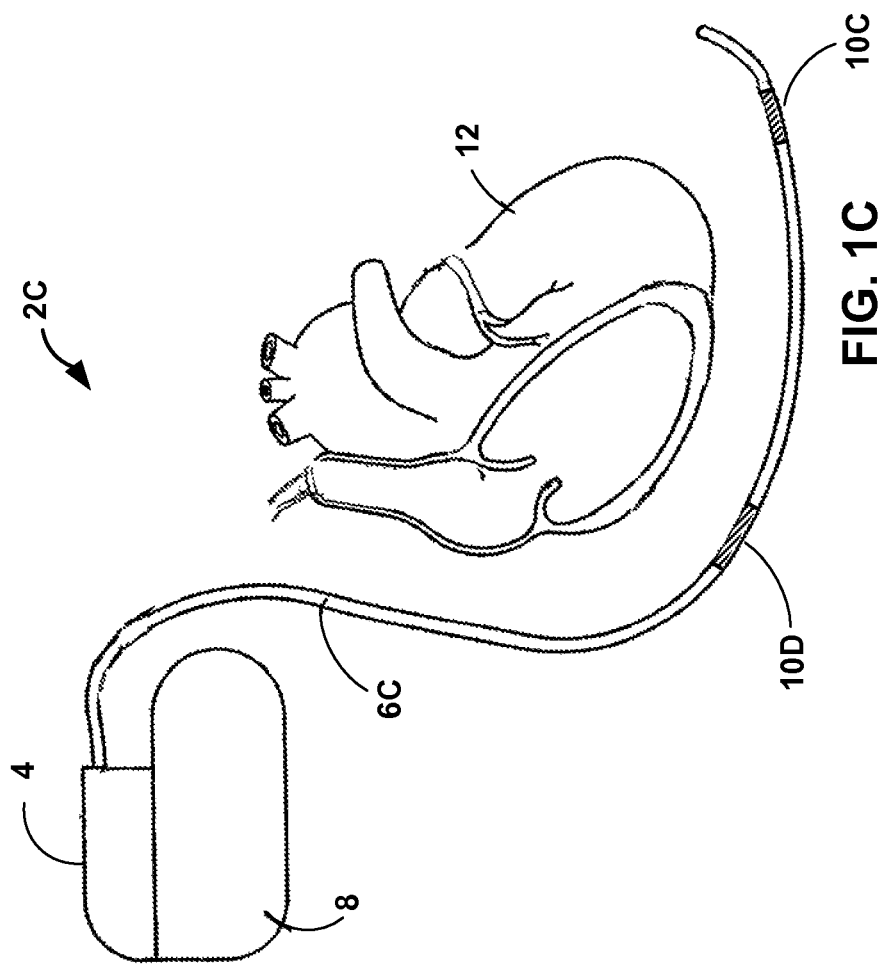

EXTRAVASCULAR ARRHYTHMIA INDUCTION

TECHNICAL FIELD

The disclosure relates generally to medical devices and, in particular, to medical devices that deliver electrical stimulation.

BACKGROUND

Medical devices, such as cardiac pacemakers, cardiac defibrillators, or implantable cardioverter-defibrillators, provide therapeutic electrical stimulation to a heart of a patient via electrodes carried by one or more medical leads and/or electrodes on a housing of the medical device. The electrical stimulation may include signals such as pulses or shocks for pacing, cardioversion or defibrillation. In some cases, a medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm of the heart. For example, in some cases, an implantable medical device (IMD) or an external medical device may deliver pacing pulses to the heart of the patient upon detecting tachycardia or bradycardia or deliver cardioversion or defibrillation shocks to the heart upon detecting tachycardia or fibrillation.

A patient receiving an IMD to treat fibrillation, e.g., atrial or ventricular fibrillation, may undergo defibrillation threshold (DFT) testing in order to ensure a reasonable certainty of successful defibrillation using shock pulse energies corresponding to the output capacity of the IMD. The DFT may be performed upon implantation of the IMD within the patient. Some IMDs determine the DFT by inducing fibrillation, and subsequently delivering defibrillation shocks to verify successful defibrillation at shock energies at least a safety margin below the maximum IMD output.

SUMMARY

In general, the disclosure is directed to inducing an arrhythmia in a heart of a patient by delivering electrical stimulation via an extravascular electrode. An extravascular electrode may comprise an electrode that is not implanted within a heart of a patient or within an artery or other vasculature of the patient. For example, an extravascular electrode may comprise an extrathoracic electrode or a subcutaneous electrode. An arrhythmia may be induced for purposes of defibrillation threshold testing upon implantation of an implantable cardioverter defibrillator (ICD) in the patient. The systems, devices, and techniques described in this disclosure for inducing an arrhythmia by delivering electrical stimulation via extravascular electrodes may be particularly useful in subcutaneous ICD systems that do not include intravascular leads. In some examples, the arrhythmia may be induced with the aid of an external device, such as an external defibrillator. Inducing an arrhythmia in a patient with the external device may provide an alternative to intravascular arrhythmia induction and/or help prolong the battery life of the ICD by displacing the generation and delivery of the arrhythmia induction electrical stimulation waveforms to a device other than the ICD.

In one aspect, the disclosure is directed to a method comprising discharging an energy storage module to generate a cardiac pacing pulse, delivering the pacing pulse to a patient via an extravascular electrode, discharging the energy storage module further to generate a cardiac shock pulse, and delivering the shock pulse to the patient via the extravascular electrode after a predetermined time period has elapsed since the delivery of the pacing pulse. The shock pulse is configured to induce an arrhythmia in the heart of the patient In another aspect, the disclosure is directed to a system comprising an extravascular electrode, a therapy module comprising an energy storage module, and a processor that controls the therapy module to discharge the energy storage module to generate a cardiac pacing pulse, deliver the pacing pulse to a patient via the extravascular electrode, discharge the energy storage module further to generate a cardiac shock pulse, and deliver the shock pulse to the patient via the extravascular electrode after a predetermined time period has elapsed since the delivery of the pacing pulse. The shock pulse is configured to induce an arrhythmia in the heart of the patient In another aspect, the disclosure is directed to a system comprising means for discharging an energy storage module to generate a cardiac pacing pulse, means for delivering the pacing pulse to a patient via an extravascular electrode, means for discharging the energy storage module further to generate a cardiac shock pulse, and means for delivering the shock pulse to the patient via the extravascular electrode after a predetermined time period has elapsed since the delivery of the pacing pulse. The shock pulse is configured to induce an arrhythmia in the heart of the patient.

In another aspect, the disclosure is directed to a method comprising generating a pacing pulse from energy stored within an energy storage module, generating a shock pulse from the energy stored within the energy storage module, delivering the pacing pulse to a patient via an extravascular electrode, and delivering the shock pulse to the patient via the extravascular electrode after delivering the pacing pulse to the patient. The shock pulse is configured to induce an arrhythmia in the heart of the patient.

In another aspect, the disclosure is directed to a method comprising generating a burst of pulses comprising a plurality of pulses from energy stored within an energy storage module, and delivering the burst of pulses via an extravascular electrode to a heart of a patient. The burst of pulses is configured to induce an arrhythmia in a heart of a patient.

In another aspect, the disclosure is directed to a system comprising an extravascular electrode, a therapy module comprising an energy storage module, and a processor that controls the therapy module to deliver a burst of pulses comprising a plurality of pulses to a patient via the extravascular electrode. The burst of pulses is configured to induce an arrhythmia in the heart of the patient. The energy storage module discharges to provide energy to the therapy module to generate the plurality of pulses.

In another aspect, the disclosure is directed to a system comprising means for generating a burst of pulses comprising a plurality of pulses from energy stored within an energy storage module, and means delivering the burst of pulses via an extravascular electrode to a heart of a patient. The burst of pulses is configured to induce an arrhythmia in a heart of a patient.

In another aspect, the disclosure is directed to a computer-readable medium and/or a computer program comprising instructions. The instructions cause a programmable processor to perform any one or more of the techniques described herein.

The details of one or more aspects of the disclosure are set forth in the accompanying drawings and the description below. Other features, objects, and advantages of the disclosure will be apparent from the description and drawings, and from the claims.

BRIEF DESCRIPTION OF DRAWINGS

FIG. 1C is a conceptual illustration of an example medical system including an IMD and a lead that includes two electrodes.

DETAILED DESCRIPTION

Figure 1A:
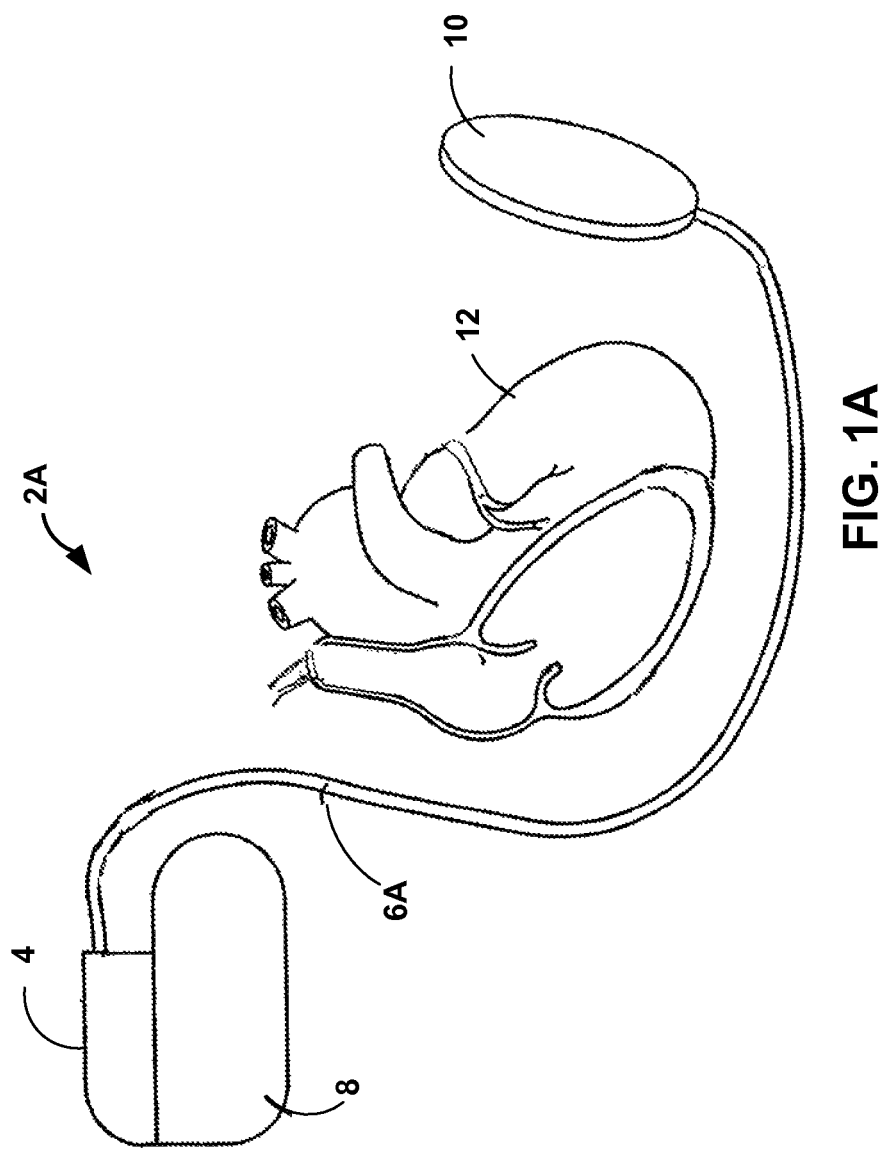
FIG. 1A is a conceptual illustration of an example medical system including an implantable medical device (IMD) and an associated lead including a subcutaneous electrode.

In some cases, an arrhythmia, e.g., atrial or ventricular fibrillation, may be induced in a patient, e.g., as part of defibrillation threshold (DFT) testing that occurs upon implantation of an implantable cardioverter-defibrillator (ICD). For example, a clinician may induce a ventricular fibrillation and subsequently deliver defibrillation shocks with the ICD to determine whether the ICD reliably defibrillates the heart and/or to determine the defibrillation thresholds (e.g., energy thresholds) that successfully terminate the ventricular fibrillation. Intravascular electrodes that are coupled to ICDs are typically used to induce arrhythmia in the patient during the DFT. The intravascular electrodes may be positioned within the heart of the patient or within an artery or other vasculature of the patient. In accordance with this disclosure, however, it may be desirable to induce an arrhythmia using an extravascular electrode, such as a subcutaneous electrode or an external electrode, rather than an intravascular electrode. Extravascular electrodes are not implanted within a chamber of a patient's heart, nor in a blood vessel or other vasculature of the patient. Useful stimulation waveforms for inducing arrhythmia in a patient via extravascular electrodes are described herein.

As described in further detail below, inducing an arrhythmia via one or more extravascular electrodes may be particularly useful in subcutaneous ICD systems that do not utilize intravascular leads. As another example, inducing an arrhythmia using an external device, e.g., an external device dedicated to arrhythmia induction, an external defibrillator, an external defibrillator controlled by a programmer, an external programmer enhanced with arrhythmia induction capabilities or an external combination programmer-defibrillator device, in a patient with an ICD may provide an alternative to intravascular arrhythmia induction, as well as help prolong the battery life of the ICD.

Some ICD systems do not utilize intravascular leads for sensing cardiac signals and delivering defibrillation shocks. Instead, these ICD systems may include, for example, a subcutaneous electrode positioned within a subcutaneous tissue layer of a patient. Accordingly, these ICD systems may be referred to as "subcutaneous" ICD systems. In some cases, the defibrillation shocks may be delivered between a subcutaneous electrode and a housing of the ICD or between two or more subcutaneous electrodes. Subcutaneous ICD systems may not include arrhythmia induction capabilities. As such, it may be necessary or desirable to induce fibrillation without the use of intravascular leads to allow DFT testing, for example, during subcutaneous ICD system implantation. Electrodes of subcutaneous ICD systems are positioned outside of the heart, i.e., extravascularly. Accordingly, more power and/or energy may be required to induce an arrhythmia in the heart with subcutaneous electrodes compared to intravascular electrodes.

In examples in which an ICD includes one or more intravascular electrodes, extravascular arrhythmia induction utilizing an external device may also be used as a back-up or alternative to induction using an intravascular electrode of the ICD system. For example, an external device with arrhythmia induction capabilities may be used as a back-up if intravascular induction attempts via the intravascular electrodes are unsuccessful. Additionally, such external devices may provide an alternative to physicians who are unsatisfied with the efficacy of intravascular induction via the ICD and intravascular electrodes. Inducement of an arrhythmia with an external device may also help prolong the battery life of the ICD, particularly in cases in which a large amount of energy may be required to induce arrhythmia in the heart of the patient. The external device may comprise an external defibrillator. An external defibrillator with arrhythmia induction capabilities may be particularly desirable, since an external defibrillator may be provided as a back-up defibrillator during DFT testing in the event defibrillation of the induced fibrillation is unsuccessful using the ICD.

Electrodes associated with external devices may be positioned on a surface, e.g., epidermis, of a patient. Accordingly, more power and/or energy may be required to induce an arrhythmia with external electrodes compared to intravascular and subcutaneous electrodes. Additionally, the stimulation parameter values for inducing the arrhythmia with the external electrodes may be selected based on the position of the electrodes with respect to the patient's skeletal muscle. For example, stimulation parameters may be configured to induce one continuous tetanic skeletal muscle contraction rather than a series of individual contractions. Skeletal muscle contractions may incidentally result from the delivery of electrical stimulation via external electrodes. The patient may perceive pain from the skeletal muscle contractions or the contractions may be disruptive to the medical device implantation process or to the arrhythmia induction process. By limiting the number of skeletal muscle contractions that may occur, e.g., inducing one continuous tetanic contraction rather than a series of shorter, individual skeletal muscle contractions, pain to the patient or disruption of the medical device implantation process or the arrhythmia induction resulting from skeletal muscle contractions may be minimized.

A sequence of stimulation pulses may be delivered to a patient via one or more extravascular electrodes to induce an arrhythmia. As one example, a stimulation generator may generate and deliver a pacing pulse configured to excite (or capture) the heart of the patient and deliver a shock pulse configured to induce an arrhythmia in the heart of the patient after a predetermined time period has elapsed since the delivery of the pacing pulse. The stimulation generator may include an energy storage module that provides the energy for generating both the pacing and shock pulses. In some examples, the pacing and shock pulses of an arrhythmia inducing waveform are generated from energy stored within the energy storage module without interim charging of the energy storage module. In some examples, both the pacing and shock pulses may be delivered as the energy storage module of the stimulation generator discharges.

In other examples, the sequence of stimulation pulses may comprise a burst of pulses configured to induce an arrhythmia in the heart of a patient. The pulses of the burst of pulses may be generated from energy stored within an energy storage module. In some examples, the pulses may be generated as the energy storage module dissipates, such that the pulses of the burst have progressively smaller amplitudes (e.g., voltage or current amplitudes). In other examples, the pulses may be generated as the energy storage module charges, such that the pulses of the burst may have progressively greater amplitudes (e.g., voltage or current amplitudes).

FIG. 1A is a conceptual illustration of an example medical system 2A that may be used to deliver cardioversion and defibrillation shocks to a heart 12 of a patient. Medical system 2A includes an implantable medical device (IMD) 4 and an associated lead 6A including a subcutaneous electrode 10A. IMD 4 may be, for example, an implantable cardiac stimulator 4 that includes a device housing 8. In some examples, lead 6A may be implanted within a subcutaneous tissue layer of a patient, e.g., within the left chest, on the back, or any other suitable region within the patient.

In some examples, lead 6A may include a subcutaneous plate electrode 10A. In other examples, lead 6A may include any other type of subcutaneous electrode, such as subcutaneous ring electrodes, subcutaneous coil electrodes, subcutaneous patch or pad electrodes, and the like, as well as any suitable number of subcutaneous electrodes, e.g., more than two subcutaneous electrodes. Electrode 10A may be located proximal the left ventricular cavity on the patient's chest, on the patient's side or back, or any other portion of the body appropriate for providing electrical stimulation to the heart. Similar electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

As further alternatives, electrode 10A may include a submuscular electrode, an epicardial electrode, or an intramural electrode. Electrical stimulation (e.g., defibrillation shocks) may be delivered to heart 12 between electrode 10A and device housing 8, e.g., between electrode 10A and housing 8 itself or between electrode 10A and an electrode on housing 8. Defibrillation shocks may have any suitable waveform (e.g., a biphasic truncated exponential) and any suitable energy level. In some examples, a defibrillation shock may have an energy of about 100 Joules to about 360 Joules, although other shocks energies are contemplated. In other examples, system 2A may comprise more than one extravascular electrode and electrical stimulation may be delivered between the extravascular electrodes.

Figure 1B:
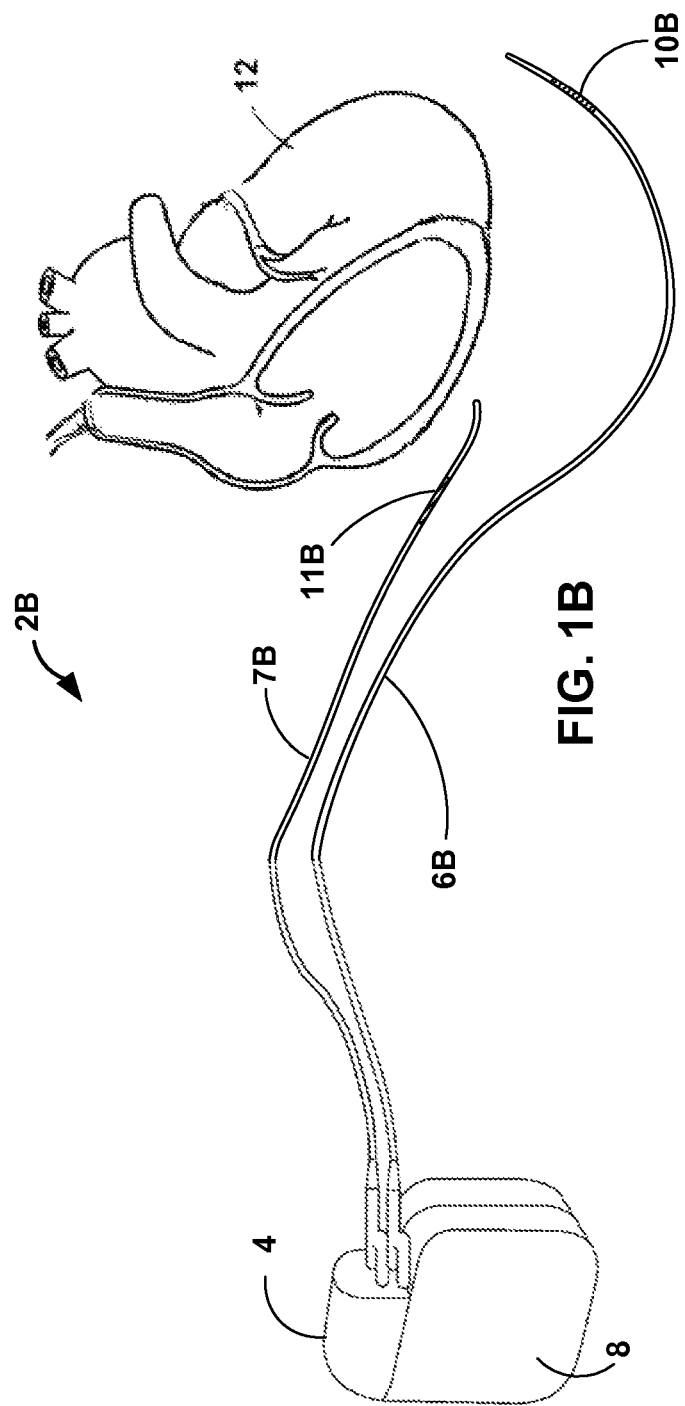
FIG. 1B is a conceptual illustration of an example medical system including an IMD and two leads that each include an electrode.

FIG. 1B is a conceptual illustration of an another example medical system 2B that may be used to deliver cardioversion and defibrillation shocks to a heart 12 of a patient. In addition, system 2B may be used to deliver stimulation pulses to induce an arrhythmia in heart 12. System 2B is substantially similar to system 2A of FIG. 1A but includes two leads 6B and 7B including electrodes 10B and 11B, respectively. In the example of FIG. 1B, electrodes 10B and 11B may be subcutaneous coil electrodes, although other types of extravascular electrodes are contemplated. Leads 6B, 7B may be electrically coupled to stimulation modules, and, in some cases, sensing modules, that are enclosed within housing 8 of IMD 4. Electrical stimulation (e.g., defibrillation shocks) may be delivered to heart 12 between electrodes 10B and 11B, e.g., in a bipolar configuration. As described in further detail below, stimulation pulses may be delivered to heart 12 via electrodes 10B, 11B in order to induce an arrhythmia in heart 12.

FIG. 1C is a conceptual illustration of another example medical system 2C that may be used to deliver cardioversion and defibrillation shocks to a heart 12 of a patient. In addition, system 2C may be used to deliver stimulation pulses to induce an arrhythmia in heart 12. System 2C is substantially similar to system 2A of FIG. 1A but includes lead 6C with two electrodes 10C and 10D. Lead 6C may be electrically coupled to a stimulation module, and, in some cases, a sensing module, that is enclosed within housing 8 of IMD 4. In the example of FIG. 1C, electrodes 10C and 10D may be subcutaneous coil electrodes, although other types of extravascular electrodes are contemplated. Electrical stimulation (e.g., defibrillation shocks) may be delivered to heart 12 between electrodes 10C and 10D, e.g., in a bipolar configuration.

In other examples, systems that may be used to deliver cardioversion and defibrillation shocks to a heart 12, as well as pulses to induce an arrhythmia, may include any suitable number of electrodes and leads. The example systems shown in FIGS. 1A-1C are merely examples of electrode configurations that may be used to deliver the electrical stimulation.

Figure 2:
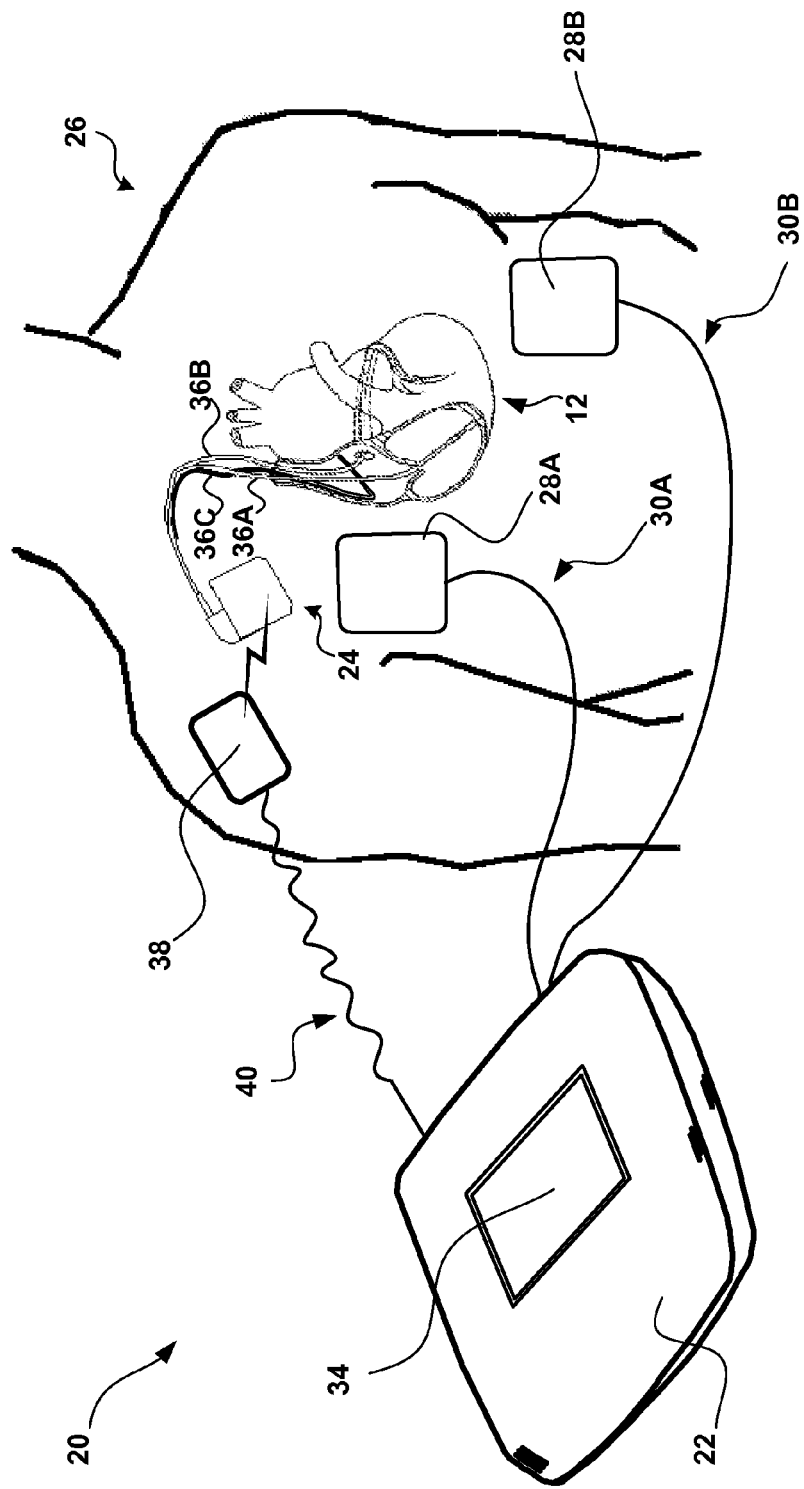
FIG. 2 is a conceptual illustration of an example system that includes an external device and an IMD implanted within a patient.

FIG. 2 is a conceptual diagram illustrating an example system 20 that includes an external stimulation device 22 and IMD 24 implanted within a patient 26. In the illustrated example, external device 22 comprises an external defibrillator. An external defibrillator with arrhythmia induction capabilities may be particularly desirable, because an external defibrillator may provide as a back-up defibrillator during DFT testing in the event defibrillation is unsuccessful using IMD 24. For example, following implantation of IMD 24 within patient 26, a clinician may initiate inducement of a ventricular fibrillation of heart 12 in order to determine whether IMD 24 may effectively terminate the fibrillation. If IMD 24 does not effectively terminate the fibrillation, external device 22 may be used to defibrillate heart 12.

External device 22 is not limited to an external defibrillator. In other examples, external device 22 may be any type of external device capable of delivering electrical stimulation to patient 26. For example, external device 22 may be a dedicated device such that the primary purpose of external device 22 is arrhythmia induction. External device 22 may also take the form of an enhanced programmer that, in addition to programming or reprogramming the operating parameters of IMD 24, may deliver electrical stimulation to patient 26. In some examples, external device 22 may include the functionality of an external programmer and an external defibrillator. As another alternative, in some cases, an external programmer may control external device 22. Furthermore, the features described with respect to external device 22 of FIG. 2 are for purposes of example. Other examples of external device 22 may include fewer or additional features.

In the illustrated example, external device 22 is coupled to two electrodes 28A and 28B (collectively "electrodes 28") that are applied to the surface, e.g., skin or epidermis, of patient 26. Electrodes 28 may be configured to deliver electrical stimulation to patient 12. In addition, in some examples, electrodes 28 may be configured to sense cardiac signals of heart 12 of patient 26, such as electrocardiogram (ECG) signals.

In some examples, electrodes 28 may comprise electrodes pads, which may include, for example, an adhesive backing for attachment to the external surface of patient 26, as is known in the art. Electrodes 28 are coupled to external device 22 by respective leads or cables 30A and 30B (collectively "cables 30"). Although illustrated in FIG. 2 as coupled to two electrodes 28, external device 22 may be coupled to any number of electrodes 28, which may be incorporated into common electrode pads and/or may share common cables 30 or may be incorporated into different electrode pads and/or be coupled to different cables 30. External device 22 may additionally or alternatively be coupled to sensors (not shown in FIG. 2) that are configured to monitor one or more physiological parameters of patient 26. Examples of sensors include, but are not limited to, blood oxygen saturation sensors or noninvasive blood pressure sensors.

As shown in FIG. 2, external device 22 may include a display 34, and may provide instructions in the form of prompts and other information to a user via the display. External device 22 may, for example, display an electrocardiogram (ECG) generated based on the electrical activity of heart 12 detected by electrodes 28 via display 34. In some examples in which external device 22 is coupled to additional sensors for sensing other physiological parameters of patient 26, and external device 22 may display current or average values for the additional parameters via display 34.

In the illustrated example, IMD 24 comprises an implantable cardioverter-defibrillator (ICD) coupled to leads 36A-36C (collectively "leads 36") that extend to selected positions within heart 12. IMD 24 may deliver cardioversion and/or defibrillation shocks to heart 12 via electrodes of leads 36, i.e., intravascular electrodes. Further, IMD 24 may sense electrical activity of heart 12 via electrodes of leads 36. Leads 36 may include any of a variety of types of electrodes (not shown) known in the art for use in sensing cardiac electrical activity and delivering stimulation to heart 12. For example, leads 36 may comprise one or more ring and/or coil electrodes. The numbers and positions of leads 36 depicted in FIG. 2 are merely exemplary. Further, the invention is not limited to systems 20 in which IMD 24 comprises an ICD. IMD 24 may comprise any type of IMD that is capable of delivering stimulation to heart 12 of patient 26 via intravascular or extravascular electrodes.

In some examples, external device 22 wirelessly communicates with IMD 24, i.e., without being coupled to IMD 24 by a wire or other electrical conductor. For example, in some examples, external device 22 wirelessly communicates with IMD 24 via a telemetry module of IMD 24, which may also be used by an external programmer to communicate with IMD 24. External programmers may communicate with IMD 24 via respective telemetry modules in order to, for example, program or reprogram the operating parameters of IMD 24, or to retrieve information stored or collected by IMD 24, as is known in the art. Like external programmers, external device 22 may include a corresponding telemetry module to facilitate communication with IMD 24. The telemetry module of external device 22 and IMD 24 may include transceivers and antennas for communication via a radio-frequency (RF) communication medium, e.g., for communication via RF telemetry. As an alternative, an external programmer may communicate with IMD 24 indirectly through external device 22.

In the example illustrated by FIG. 2, external device 22 is coupled to a telemetry head 38 by a cable 40. Telemetry head 38 may include an antenna, and may be placed proximate to, e.g., over, IMD 24 by a user of external device 22 to enable external device 22 to detect and communicate with IMD 24. In some examples, external device 22 may be removably coupled to telemetry head 38 by cable 40. In other examples, telemetry head 38 may be integral with a housing of external device 22, or incorporated into one of electrodes 28 and coupled to external device 22 by a lead 30.

In other examples, the telemetry circuitry and antennae of external device 22 and IMD 24 may support a signal strength, other signal characteristics, and communication protocol that allow RF telemetry communication between external device 22 and IMD 24 at relatively greater distances. In such examples, one or more antennae of external device 22 may be housed within external device 22, i.e., external device 22 need not be coupled to telemetry head 38 to communicate with IMD 24, and external device 22 may detect and communicate with IMD 24 when brought into proximity with IMD 24.

Figure 3A:
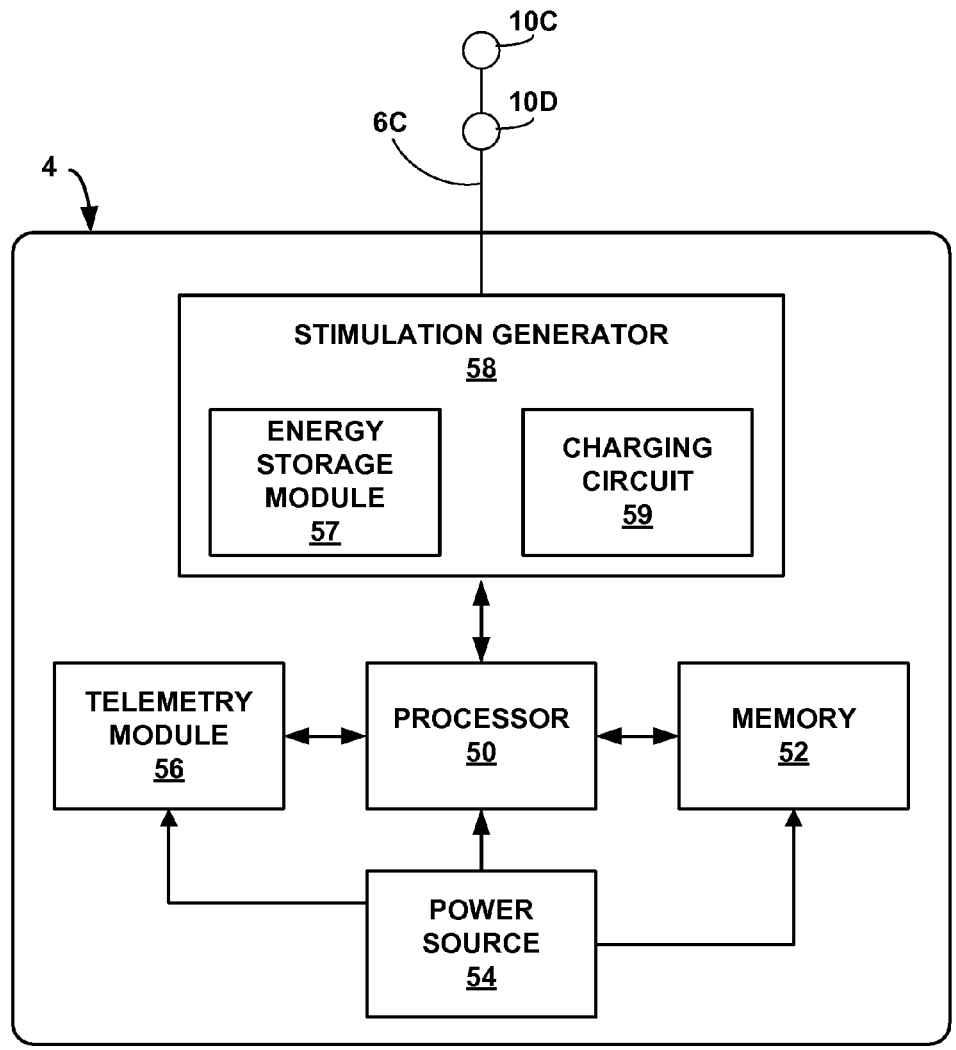
FIG. 3A is an example functional block diagram of the IMD of FIG. 1C.

FIG. 3A is an example functional block diagram of IMD 4 of FIG. 11C. In the example illustrated in FIG. 3A, IMD 4 includes processor 50, memory 52, power source 54, telemetry module 56, and stimulation generator 58. As shown in FIG. 3A, stimulation generator 58 is electrically coupled to electrode 10C and 10D via lead 6C. Although FIG. 3A illustrates the lead 6C of FIG. 1C coupled to stimulation generator 58, in other examples, lead 6A (FIG. 1A), lead 6B, lead 7B (FIG. 1B) or any other lead comprising one or more electrodes may be coupled to stimulation generator. For example, stimulation generator 58 may be configured to deliver stimulation via electrode 10A (FIG. 1A) and housing 8 (in examples in which housing 8 is conductive) or an electrode on housing 8. In addition, although electrodes 10C, 10D are described as subcutaneous electrodes, in other examples, electrodes 10C, 10D may be positioned in another tissue layer of patient other than the subcutaneous tissue layer.

Memory 52 includes computer-readable instructions that, when executed by processor 50, cause IMD 4 and processor 50 to perform various functions attributed to IMD 4 and processor 50 herein. Memory 52 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Stimulation generator 58 produces stimulation signals (e.g., pulses or continuous time signals, such as sine waves) for delivery to a patient via subcutaneous electrodes 10C and 10D carried by lead 6C. Processor 50 controls stimulation generator 58 to apply particular stimulation parameter values specified by at least one program (e.g., programs stored within memory 52). For example, the program may define respective values for an electrode combination, electrode polarities, amplitude, pulse width, and pulse rate of the stimulation signals. Processor 50 may include any one or more microprocessors, controllers, digital signal processors (DSPs), application specific integrated circuits (ASICs), field-programmable gate arrays (FPGAs), or equivalent discrete or integrated logic circuitry, or combinations thereof. In some examples, processor 50 may include multiple components, such as any combination of one or more microprocessors, one or more controllers, one or more DSPs, one or more ASICs, or one or more FPGAs, as well as other discrete or integrated logic circuitry. The functions attributed to processor 50 herein may be embodied as software, firmware, hardware or any combination thereof.

Stimulation generator 58 may include an energy storage module 57 and charging circuit 59. Stimulation generator 58 may also include one or more switches (not shown in FIG. 3A) that, when activated, couple energy storage module 57 to electrode 10C and 10D of lead 6C. Energy storage module 57 stores energy to be delivered to a patient in the form of stimulation signals. In some examples, energy storage module 57 may include one or more circuitry components, such as one or more capacitors, that store the energy to be delivered to the patient via electrodes 10C and 10D. The energy may be delivered to the patient, e.g., in order to induce an arrhythmia or in order to stop the arrhythmia.

In order to generate sufficient energy to deliver stimulation to the patient, energy storage module 57 may be charged. Processor 50 may control the operation of charging circuit 59, such as by directing charging circuit 59 to charge energy storage module 57 to a high voltage level, e.g., 1 kilovolt. Charging circuit 59 may comprise, for example, a flyback charger that transfers energy from power source 54 to energy storage module 57.

When the energy stored in energy storage module 57 reaches the desired energy level of the stimulation output, processor 50 may control stimulation generator 58 to deliver stimulation to the patient using a specified set of stimulation parameter values. For example, processor 50 may activate the switches of stimulation generator 58 to electrically connect energy storage module 57 to electrode 10C and 10D of lead 6C, and thereby deliver stimulation to the patient while discharging energy storage circuit 57. Stimulation generator 58, energy storage module 57, and charging circuit 59 are examples of therapy delivery circuitry that deliver therapy to a patient under control of processor 50. In other examples, IMD 4 may include other types and configurations of therapy delivery circuitry.

Processor 50 may modulate the stimulation signal delivered to the patient via stimulation generator 58. Processor 50 may, for example, control the switches of stimulation generator 58 to regulate the shape and width of a stimulation pulse. Processor 50 may control the switches to modulate the pulse, for example, to provide a multiphasic pulse, such as a biphasic truncated exponential pulse.

In addition to delivering stimulation therapy to heart 12 (FIGS. 1A-2) of a patient, stimulation generator 58 may be used to generate stimulation signals to induce an arrhythmia in heart 12 of a patient. For example, processor 50 may control charging circuit 59 to charge energy storage module 57 to a voltage level sufficient to deliver one or more stimulation pulses configured to induce an arrhythmia in the patient. Processor 50 may control stimulation generator 58 to deliver one or more stimulation pulses according to stimulation parameter values, e.g., amplitude, pulse width, timing of pulses, and number of pulses, specified by an arrhythmia induction program, e.g., a program stored within memory 52. As described in further detail with respect to FIGS. 5-7, processor 50 may control the switches of stimulation generator 58 to modulate the pulse, for example, to provide a monophasic untruncated exponential pulse, monophasic truncated exponential pulse, biphasic truncated exponential pulse, or biphasic symmetric pulse.

In some cases, the stimulation pulses delivered to induce arrhythmia may be limited by the storage capacity of energy storage module 57. Processor 50 may control stimulation generator 58 to deliver a sequence of pulses to the patient as energy storage module 57 discharges. Stimulation generator 58 may generate the pulses of the sequence of pulses from energy stored within energy storage module 57. Energy storage module 57 may store a finite amount of energy, and, in some examples, stimulation generator 58 may generate the pulses of the sequence of pulses with the finite amount of energy available within energy storage module 57, e.g., without interim charging of energy storage module 57. That is, energy storage module 57 may not be recharged between the generation and delivery of pulses of the sequence of pulses, whether the pulses include pacing pulses, shock pulses or a burst of pulses. In other examples, energy storage module 57 may be recharged between the generation and delivery of pulses of the sequence of pulses.

In some examples, as described with respect to FIGS. 5A-6B, processor 50 may control stimulation generator 58 to deliver a pacing pulse configured to excite heart 12, e.g., to evoke a ventricular contraction, and deliver a shock pulse configured to induce an arrhythmia in heart 12 after a predetermined time period has elapsed since the delivery of the pacing pulse. In some examples, both the pacing and shock pulses may be delivered as energy storage module 57 discharges and without further charging of energy storage module 57. As another example, as described below with respect to FIGS. 7A and 7B, processor 50 may control stimulation generator 58 to deliver a burst of pulses configured to induce an arrhythmia in heart 12 as energy storage module 57 discharges.

Telemetry module 56 supports wireless communication between IMD 4 and an external programmer or another computing device under the control of processor 50. In some examples, telemetry module 56 may include a transmitter and receiver to permit bi-directional communication between IMD 4 and an external device. Processor 50 of IMD 4 may receive, as updates to programs, values for various stimulation parameters, such as pulse widths and timing between pulses configured to induce an arrhythmia in heart 12, from an external programmer or other computing device. The updates to the therapy programs or arrhythmia induction programs may be stored within memory 52. Additionally, processor 50 may send status and operational information to an external programmer via telemetry module 56.

The various components of IMD 4 are coupled to power source 54, which may include a rechargeable or non-rechargeable battery. A non-rechargeable battery may be selected to last for several years, while a rechargeable battery may be inductively charged from an external device, e.g., on a daily or weekly basis. In other examples, power source 54 may be powered by proximal inductive interaction with an external power supply carried by the patient.

Figure 3B:
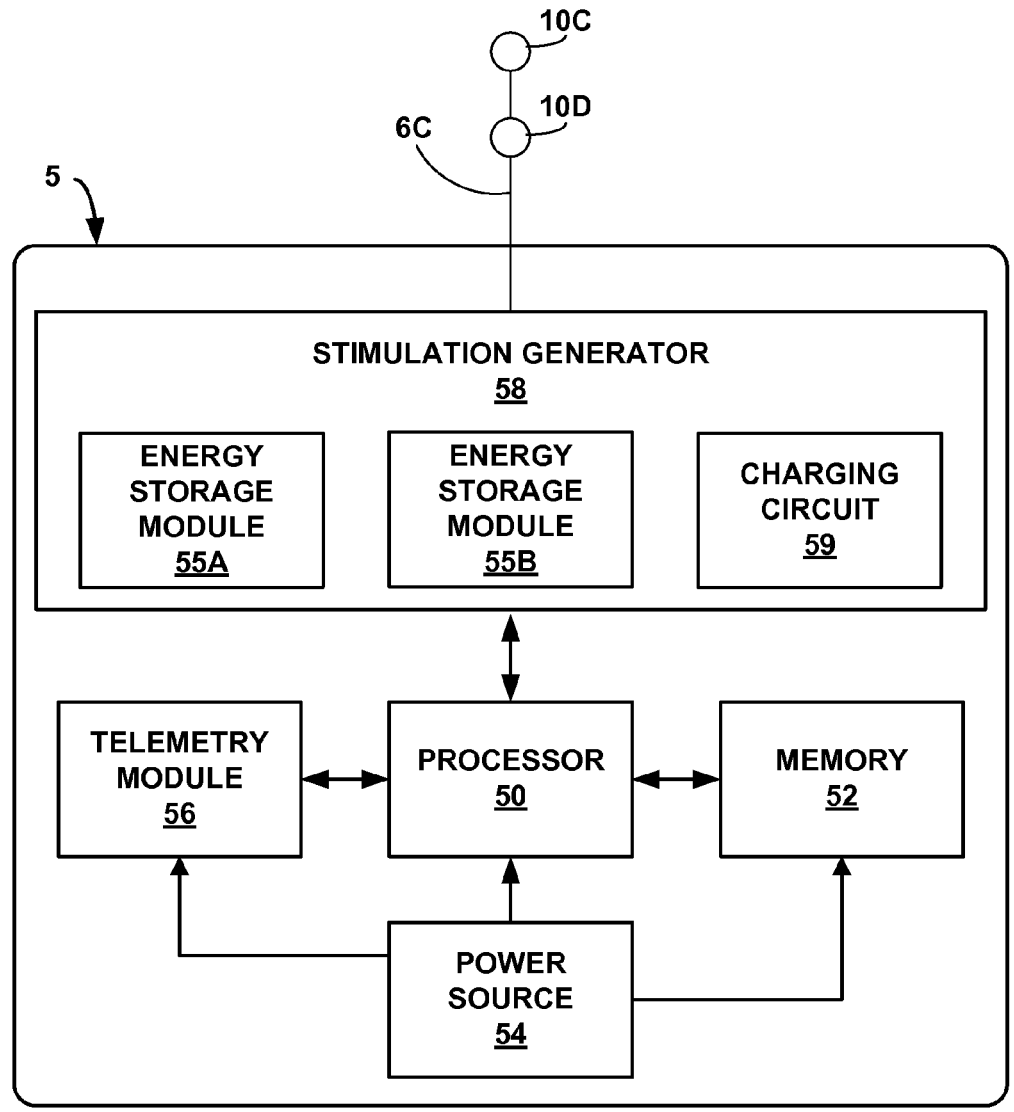
FIG. 3B is an example functional block diagram of another example IMD.

FIG. 3B is an example functional block diagram of another example IMD 5 (FIGS. 1A-1C). IMD 5 is substantially similar to IMD 4 of FIG. 3A but includes two energy storage modules 55A and 55B (collectively "energy storage modules 55"). Energy storage modules 55 may each be similar to energy storage module 57 of IMD 4. As described in further detail below, energy storage modules 55 may be used to generate different types of stimulation pulses. For example, processor 50 may control energy storage module 55A to deliver pacing pulses, and processor 50 may control energy storage module 55B to deliver shock pulses and/or defibrillator shocks. In this way, the pacing pulses and the shock pulses may be generated with energy from different energy storage modules 55.

Figure 4:
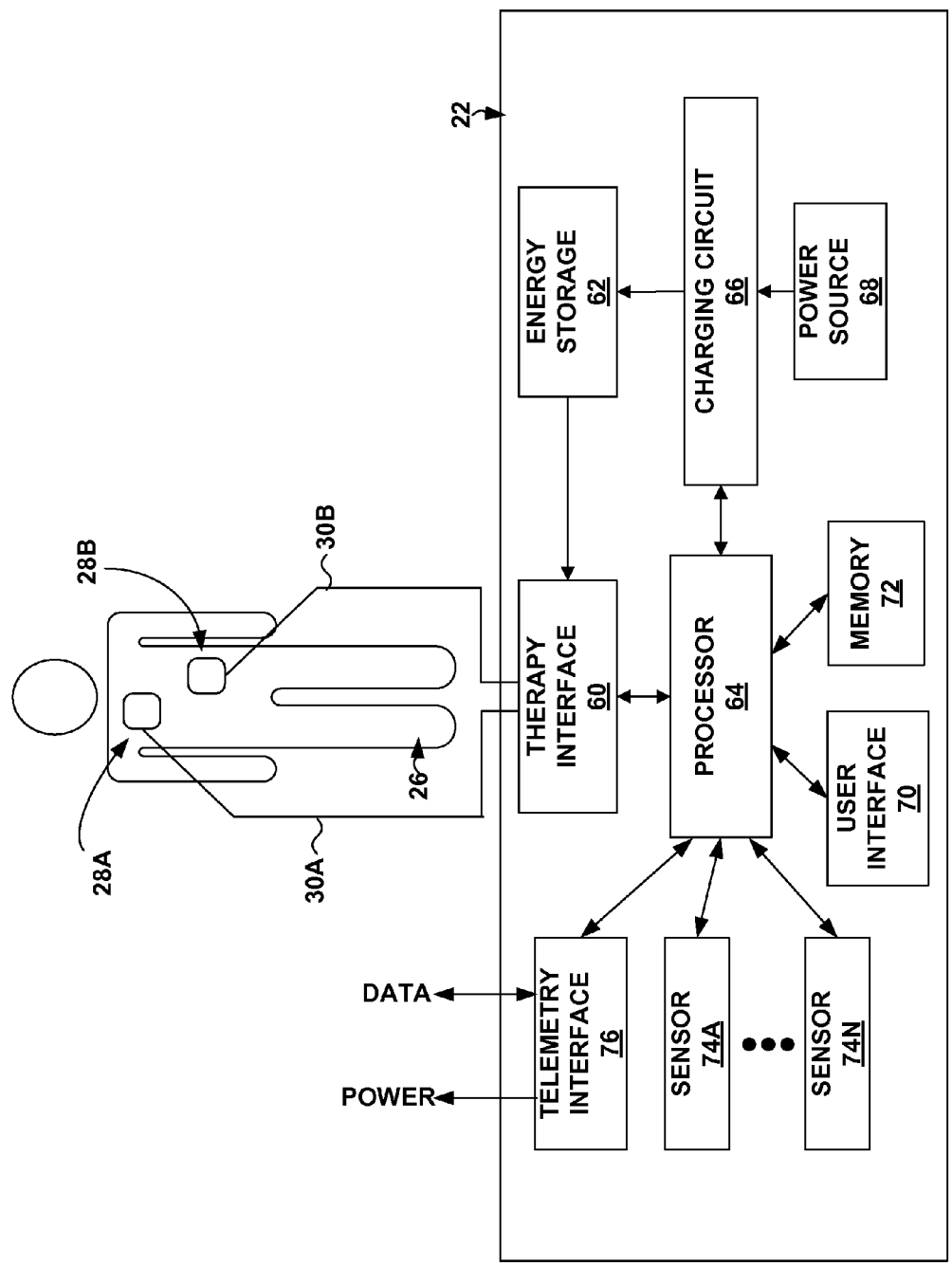
FIG. 4 is an example functional block diagram of the external device of FIG. 2.

FIG. 4 is a functional block diagram further illustrating external device 22 of FIG. 2. External defibrillator comprises therapy interface 60, energy storage module 62, processor 64, charging circuit 66, power source 6, user interface 70, memory 72, sensors 74A-74N (collectively referred to as "sensors 74"), and telemetry interface 76. In FIG. 4, external device 22 is shown coupled to patient 26 by electrodes 28 and corresponding cables 30, as described above. In some examples, therapy interface 60 of external device 22 may include a receptacle that is configured to receive cables 30.

Therapy interface 60 includes a switch (not shown in FIG. 4) that, when activated, couples energy storage module 62 of external device 22 to electrodes 28 via cables 30. Energy storage module 62 stores energy to be delivered to patient 26 in the form of a stimulation pulse. As described in further detail below, the stimulation pulses may comprise pacing pulses as well as defibrillation shocks. The switch may be of conventional design and may comprise, for example, of electrically operated relays. Alternatively, the switch may comprise an arrangement of solid-state devices such as silicon-controlled rectifiers or insulated gate bipolar transistors.

Energy storage module 62 includes components, such as one or more capacitors, that store the energy to be delivered to patient 26 via electrodes 28. Energy storage module 62 is charged before one or more stimulation pulses are delivered to patient 26. Processor 64 may control charging circuit 66 to charge energy storage module 62 to a high voltage level. Charging circuit 66 may comprise, for example, a flyback charger that transfers energy from a power source 68 to energy storage module 62.

In some examples, external device 22 may be a manual defibrillator or an automatic external defibrillator (AED). In examples in which external device 22 is a manual defibrillator, a user of external device 22 may select an energy level for each defibrillation shock delivered to patient 26. The energy levels of the defibrillation shocks will typically be substantially higher than the energy levels of the pacing pulses. Processor 64 may receive the selection made by the user via a user interface 70, which may include input devices, such as a keypad and various buttons or dials, and output devices, such as various indicator lights, display 34 (FIG. 2), and a speaker. Display 34 may include a cathode ray tube (CRT), light emitting diode (LED), or liquid crystal display (LCD) screen.

In examples in which external device 22 is an AED, processor 64 may select an energy level for the defibrillation shocks. For example, processor 64 may select an energy level from a preprogrammed progression of energy levels stored in a memory 72 based on the number of defibrillation shocks already delivered to patient 26. In some manual defibrillator examples, processor 64 may select an energy level, e.g., based on a preprogrammed progression, to recommend to a user via user interface 70.

In either case, when the energy stored in energy storage module 62 reaches the desired energy level, processor 64 controls user interface 70 to provide an indication to the user that external device 22 is ready to deliver a defibrillation shock to patient 26, such as an indicator light or a voice prompt. The defibrillation shock may be delivered manually or automatically. In examples in which the defibrillation shock is delivered manually, the user may direct processor 64 to deliver the defibrillation shock via user interface 70 by, for example pressing a button. In either case, processor 64 activates the switches of therapy interface 60 to electrically connect energy storage module 62 to electrodes 28, and thereby deliver the defibrillation shock to patient 26. Therapy interface 60, energy storage module 62, and charging circuit 66 are examples of therapy delivery circuitry that deliver therapy to patient 26 under control of processor 64.

Processor 64 may modulate the stimulation pulses delivered to patient 26. Processor 64 may, for example, control the switches of therapy interface 60 to regulate the shape and width of the defibrillation shock. Processor 64 may control the switches to modulate the shock to, for example, provide a multiphasic waveform, such as a biphasic truncated exponential waveform.

Therapy interface 60, energy storage module 62, and charging circuit 66 may also be used to induce an arrhythmia in patient 26. For example, processor 64 may control charging circuit 66 to charge energy storage module 62 to a voltage level sufficient to deliver one or more stimulation pulses configured to induce an arrhythmia in patient 26. Processor 64 may control therapy interface 60 to deliver one or more stimulation pulses according to parameters, e.g., amplitude, pulse width, timing of pulses, and number of pulses, specified by an arrhythmia induction program, e.g., a program stored within memory 72. As described in further detail with respect to FIGS. 5-7, processor 64 may control the switches of therapy interface 60 to modulate one or more arrhythmia-inducing stimulation pulses, for example, to provide one or more monophasic untruncated exponential pulses, monophasic truncated exponential pulses, biphasic truncated exponential pulses, or biphasic symmetric pulses.

In some cases, the stimulation pulses delivered to induce arrhythmia in heart 12 of patient 26 may be limited by the storage capacity of energy storage module 62. Processor 64 may control therapy interface 60 to deliver a sequence of pulses to patient 26 as energy storage module 62 discharges. Just as with stimulation generator 58 of IMD 4 (FIG. 3A), processor 64 may control therapy interface 60 to generate a sequence of pulses from energy stored within energy storage module 62. Energy storage module 62 may store a finite amount of energy, and, in some examples, therapy interface 60 may generate the pulses of the sequence of pulses with the finite amount of energy available within energy storage module 62, e.g., without interim charging of energy storage module 62. Accordingly, in some examples, energy storage module 62 may not be recharged between the generation and delivery of pulses of the sequence of pulses. In other examples, energy storage module 62 may be charged between the generation and delivery of pulses within a sequence of pulses configured to induce an arrhythmia in heart 12 of patient 26.

In some examples, as described in further detail below with reference to FIGS. 5A-6B, processor 64 may control therapy interface 60 to deliver one or more pacing pulses configured to excite the heart of patient 26 and deliver a shock pulse configured to induce an arrhythmia in the heart of patient 26 after a predetermined time period has elapsed since the delivery of the one or more pacing pulses. Both the pacing and shock pulses may be delivered as energy storage module 62 discharges, e.g., without further charging of energy storage module 62. As another example, processor 64 may control therapy interface 60 to deliver a burst of pulses configured to induce an arrhythmia in the heart of patient 26 as energy storage module 62 discharges. An example of this technique for inducing arrhythmia in heart 12 of patient 26 is described with respect to FIGS. 7A and 7B.

Processor 64 may perform other functions as well, such as monitoring electrical activity of the heart of patient 26 sensed via electrodes 28. Therapy interface 60 may include circuitry for sensing the electrical activity of the heart via electrodes 28. Processor 64 may determine whether heart 12 of patient 26 is fibrillating based upon the sensed electrical activity in order to determine whether a defibrillation shock should be delivered to patient 26. Where a defibrillation shock has already been delivered, processor 64 may evaluate the efficacy of the delivered defibrillation shock by determining if heart 12 is still fibrillating in order to determine whether an additional defibrillation shock is warranted. Processor 64 may automatically deliver defibrillation shocks based on these determinations, or may advise the caregiver of these determinations via user interface 70. Processor 64 may display an ECG that reflects the sensed electrical activity via user interface 70, e.g., via display 34 (FIG. 2).

Processor 64 may store an indication of the time of delivery of each defibrillation shock delivered to patient 26 as medical event information within memory 72 for patient 26. Processor 64 may also store the energy level of each defibrillation shock and other characteristics of each shock, such as the width, amplitude, or shape, as medical event information for patient 26. Processor 64 may also store a digital representation of the ECG, or a heart rate over time determined based on the electrical activity of the heart of patient 26 detected via electrodes 28 within memory 72 as medical event information for patient 26. Further, processor 64 may control delivery of other types of therapy to patient 26 via electrodes 28, such as cardioversion or pacing therapy, and store information describing the times that such therapies were delivered and parameters of such therapies, such as cardioversion pulse energy levels and pacing rates, as medical event information for patient 16.

In some examples, external device 22 may also include additional sensors 74, such as sensors to measure blood oxygen saturation, blood pressure, respiration, the amount of oxygen or carbon dioxide in the air inhaled or exhaled by patient 26 or to sense other physiological parameters of patient 12. Sensors 74 may be included within or coupled to external device 22, and may be electrically coupled to processor 64. External device 22 may include circuitry that conditions the signals generated by sensors 74 such that they may be analyzed by processor 64, such as one or more analog to digital converters to, as suitable, filter and amplifier circuitry.

Processor 64 may store the signals generated by these sensors within memory 72 as medical event information for patient 26. For example, processor 64 may store any of a capnograph, a plethysmograph, a blood oxygen saturation over time, a blood pressure over time, a pulse rate over time determined based on measured blood pressure, end tidal carbon dioxide measurements, and/or measurements of the fraction of carbon dioxide in air inspired or expired within memory 72 as medical event information for patient 16. Processor 64 may also receive other information collected by a user during treatment of patient 26, such as a location of treatment or time of death, and store such information as medical event information for the patient. Processor 64 may begin to store medical event information when external device 22 is powered on to respond to a medical emergency involving patient 26.

Processor 64 may be similar to processor 50 of IMD 4 (FIG. 3A) and may include, for example, one or more microprocessors, DSPs, ASICs, FPGAs, or other logic circuitry. Memory 72 may include program instructions that cause processor 64 to perform the functions attributed to processor 64 and external device 22 herein. Accordingly, the invention also contemplates computer-readable media storing instructions to cause processor 64 to provide the functionality described herein. Memory 72 may include any of a variety of solid state, magnetic or optical media, such as RAM, ROM, CD-ROM, magnetic disk, EEPROM, or flash memory.

In the example illustrated by FIG. 4, external device 22 includes a telemetry interface 76. Telemetry interface 76 may include a port or other physical interface to receive cable 40 that is coupled to telemetry head 38 (FIG. 2), and to electrically couple the circuitry within external device 22 to the circuitry within telemetry head 38 via cable 40. Processor 64 may communicate with IMD 24 via telemetry interface 76 and telemetry head 38.

In some examples, as illustrated in FIG. 4, interface 76 may convey data between processor 64 and telemetry head 38, as well as provide power from external device 22 to power the circuitry within telemetry head 38. In some examples, telemetry head 38 may incorporate telemetry circuitry including a transceiver and one or more analog to digital and digital to analog converters, in addition to one or more antennae for communication with IMD 24. In such examples, telemetry interface 74 may include any of a variety of known digital data interfaces, such as a universal serial bus (USB) port.

In other examples, external device 22 may include the telemetry circuitry, and telemetry head 38 may include only one or more antennae for communication with IMD 24. Further, in still other examples, external device 22 may include both telemetry circuitry and antennae for communication with IMD 24. In such examples, external device 22 need not be coupled to telemetry head 38 for in order to communicate with IMD 24.

FIGS. 5A-7B illustrate example stimulation waveforms that a medical device may deliver to a patient via extravascular electrodes to induce an arrhythmia. Although, the description of FIGS. 5A-7B generally refers to arrhythmia induction by external device 22 under the control of processor 64, the disclosure is not so limited. In other examples, any medical device capable of extravascularly stimulating a patient's heart, such as an IMD of a subcutaneous ICD system (e.g., as shown in FIGS. 1A-1C), may be used to induce an arrhythmia using the example stimulation waveforms and techniques described herein.

Figure 5A:
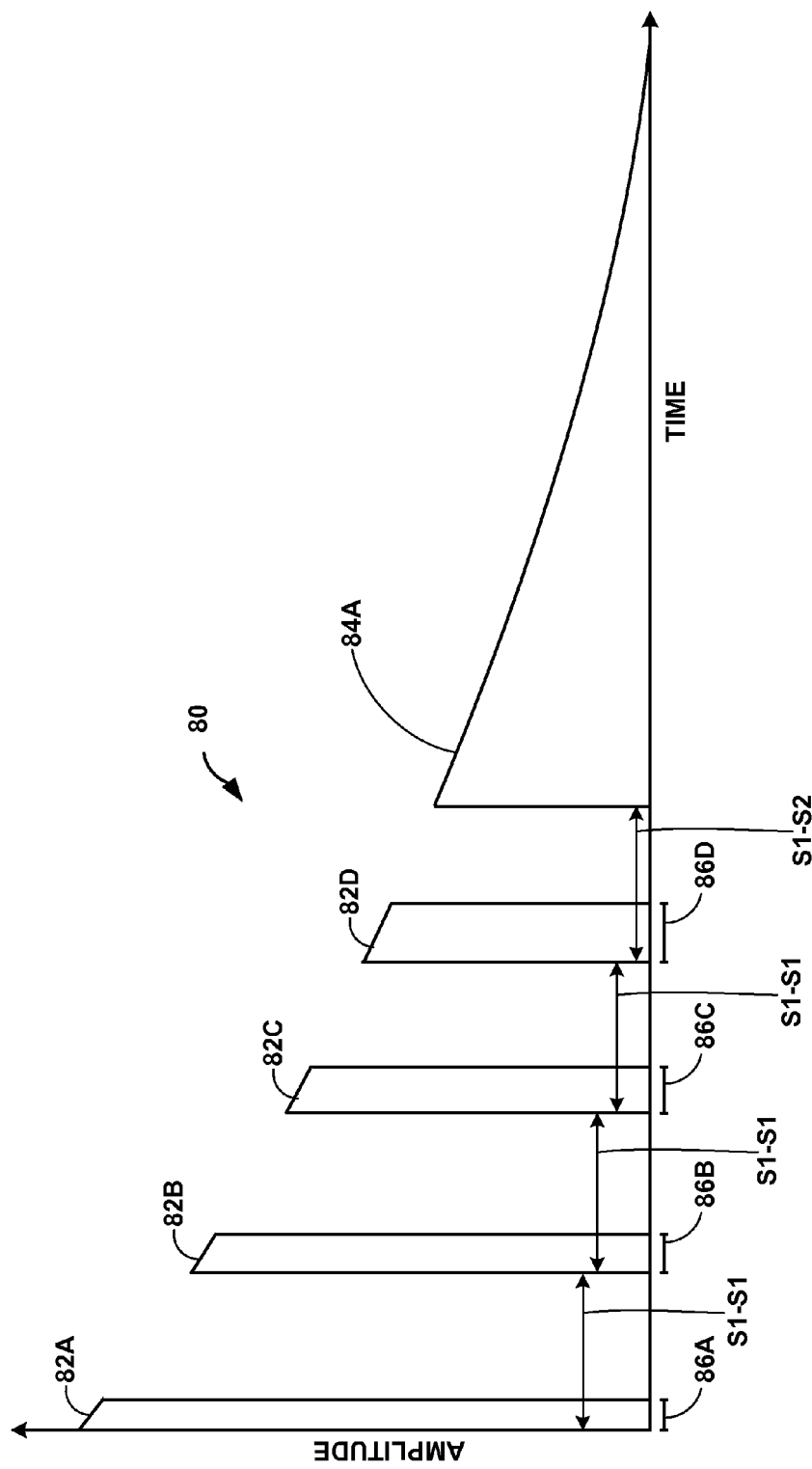
FIG. 5A is a conceptual illustration of an example waveform of electrical stimulation that a medical device may deliver to a patient via one or more extravascular electrodes to induce a cardiac arrhythmia.

FIG. 5A illustrates a waveform 80 that includes a sequence of four pacing pulses 82A-82D (collectively "pacing pulses 82") followed by a shock pulse 84A. Pacing pulses 82 may be configured to excite the heart of a patient to initiate a heartbeat, i.e., evoke a contraction of heart 12. In this manner, pacing pulses 82 may control the patient's heart rate. In some examples, pacing pulses 82 may each comprise an amplitude of about 1 kilovolt or higher. However, other stimulation parameters values for pacing pulses 82 are contemplated. Pacing pulses 82 may be used to establish a relatively stable cardiac rhythm of heart 12 in order to synchronize shock pulse 84A with the patient's cardiac rhythm. For example, processor 64 may initiate the delivery of pacing pulses 82 at constant time intervals to cause the patient's heart rate to be substantially constant. The time interval between consecutive pacing pulses 82 may be referred to as an S1-S1 interval, as indicated in FIG. 5A. The S1-S1 interval may be selected based on the known heart rhythm of patient 26, e.g., based on past ECG data or real-time EEG data, or based on the expected heart rhythm of patient 26 resulting from the delivery of pacing pulses 82.

In some examples, pacing pulses 82 may increase the patient's heart rate above the patient's intrinsic heart rate. This may be referred to as "overdrive pacing" of heart 12 (FIGS. 1 and 2). For example, the S1-S1 interval between consecutive pacing pulses 82, e.g., between the initiations of consecutive pacing pulses, may be less than approximately 500 milliseconds. This timing interval may correspond to a heart rate of greater than approximately 120 beats per minute. As another example, the S1-S1 interval between the initiation of consecutive pacing pulses may be approximately 400 milliseconds.

Although the example illustrated in FIG. 5A includes four pacing pulses 82, in other examples, waveform 80 may include a fewer number of pacing pulses or a greater number of pacing pulses. For example, waveform 80 may include approximately four to approximately eight pacing pulses. In some examples, waveform 80 may include as few as one pacing pulse. In other examples, waveform 80 may not include any pacing pulses and, instead, may only include shock pulse 84A. The shock pulse 84A may be delivered during a vulnerable period of the patient's cardiac cycle, as described in further detail below. While pacing pulses 82 may be selected such that patient 26 does not feel the delivery of stimulation, in some examples, pacing pulses 82 may cause discomfort to patient 26. Thus, in some examples, minimizing the number of pacing pulses 82 that are delivered to patient 26 prior to delivering shock pulse 84A may be desirable.

After a predetermined time period has expired since the delivery of the last pacing pulse 82D, processor 64 may initiate delivery of shock pulse 84A that is configured to induce an arrhythmia in heart 12. The predetermined time period, which may be referred to as an S1-S2 interval (shown in FIG. 5A) may be selected to synchronize shock pulse 84A with the vulnerable period of the cardiac cycle. For example, the shock pulse may be delivered during the vulnerable period of the cardiac cycle, e.g., at the same time as the vulnerable period or within a certain time range so as to coincide with the vulnerable period. The vulnerable period of the cardiac cycle may include the time period during which repolarization of the cardiac muscle is occurring, rendering heart 12 susceptible to induced fibrillation. The vulnerable period may generally correspond to the T-wave of the electrocardiogram (ECG) signal. Therefore, a shock pulse may also be referred to as a "T-shock" or "T-wave shock," and the delivery of the shock pulse may correspond in time to the occurrence of the T-wave (e.g., may occur at the same time as the T-wave). In some cases, a highest-energy shock that induces fibrillation in the heart of a patient, the Upper Limit of Vulnerability (ULV), is correlated with the DFT for the particular patient. Accordingly, delivering shock pulse 84A during the vulnerable period of the cardiac rhythm may be useful in not only increasing the probability of inducing arrhythmia, but to determine the DFT for patient 26.

When the patient's heart rate is substantially constant, the occurrence of the vulnerable period (or vulnerable zone) of the cardiac rhythm, e.g., T-wave of the ECG signal, may also be substantially constant and predictable. Pacing the patient's heart rate above the patient's intrinsic heart rate with pacing pulses 82 may also increase the consistency and predictability of the vulnerable period timing. In this manner, the delivery of pacing pulses 82 may aid in synchronizing shock pulse 84A with the vulnerable period of the cardiac cycle and, therefore, increase the likelihood of inducing arrhythmia with shock pulse 84A.

The predetermined time period between the delivery of the last pacing pulse 82D and delivery of shock pulse 84A (i.e., the S1-S2 interval shown in FIG. 5A) may vary based on the heart rate of heart 12 prior to the delivery of shock pulse 84A. Any suitable technique may be employed to time the delivery of shock pulse 84A with a vulnerable period of the patient's cardiac rhythm. In some examples, a clinician may program the S1-S2 interval into memory 72 of external device 22 (FIG. 4). In other examples, processor 64 of external device 22 (or processor 50 of IMD 4 or another device) may automatically determine the S1-S2 interval between the delivery of the last pulse 82D and shock pulse 84A based on real-time ECG data indicating the cardiac rhythm of heart 12 of patient 26 or based on past ECG data that may be stored within memory 72. The ECG data may be obtained via implanted or external electrodes.

Techniques for detecting a vulnerable period of a cardiac rhythm are described in commonly-assigned U.S. Pat. No. 7,181,275 to Havel, entitled, "METHOD AND APPARATUS FOR ACTIVELY DETERMINING A COUPLING INTERVAL CORRESPONDING TO A CARDIAC VULNERABLE ZONE," which issued on Feb. 20, 2007 and is incorporated herein by reference in its entirety.

In some examples, the predetermined time period between the delivery of the last pacing pulse 82D and delivery of shock pulse 84A may generally be less that the time interval between initiation of consecutive pacing pulses 82. That is, in some examples, the S1-S2 interval may be less than the S1-S1 intervals. In some examples, the S1-S1 time interval between initiation of consecutive pacing pulses 82 may generally correspond to the time interval between consecutive Q-waves of an ECG signal representing the cardiac activity of heart 12 of patient 26. The predetermined time period, i.e., the S1-S2 interval, between the delivery of the last pacing pulse 82D of waveform 80 and the delivery of shock pulse 84A may generally correspond to the time interval between a Q-wave and a subsequent T-wave of the ECG signal. In some examples, the S1-S2 interval may be between approximately 240 milliseconds and approximately 400 milliseconds, such as approximately 310 milliseconds. However, other time periods are contemplated.

As illustrated in FIG. 5A, the amplitude of waveform 80 may decrease over time. In some cases, the shape of waveform 80 may generally correspond to the discharge waveform of energy storage module 62 (FIG. 4). In the example shown in FIG. 5A, the sequence of pulses 82, 84A are generated from a finite amount of energy stored within energy storage module 62, e.g., without interim charging of energy storage module 62 between the delivery of some of the pulses 82, 84A. For example, processor 64 of external device (FIG. 4) may control energy storage module 62 to discharge to generate pacing pulses 82 and may control therapy interface 60 to deliver pacing pulses 82. In some cases, energy storage module 62 and therapy interface 60 may be a part of a common stimulation module. Processor 64 may then control energy storage module 62 to further discharge to generate shock pulse 84 without interim charging of energy storage module 62 between the delivery of pacing pulses 82 and the generation of shock pulse 84. However, in other examples, energy storage module 62 may be charged between the generation and delivery of at least some of the pulses 82, 84A.

The amplitude of the voltage stored by energy storage module 62 may decrease, e.g., exponentially, as energy storage module 62 is discharged and pulses 82, 84A are generated and delivered to patient 26. Processor 64 may control delivery of pacing pulses 82 and shock pulse 84A as energy storage module 62 discharges. That is, pacing pulses 82 and shock pulse 84A may be generated and delivered without the recharging of energy storage module 62, such that pacing pulses 82 and shock pulse 84A may only draw energy from the finite amount of energy stored within energy storage module 62. Each of pulses 82 and 84A may have a different amplitude because pulses 82 and 84A are delivered to patient 12 via electrodes 28 (FIG. 2) at various charge levels of energy storage module 62. Thus, as energy storage module 62 dissipates energy, the amplitude of subsequent pulses 82, 84A may decrease relative to the previously delivered pulse.

In some examples, it may be desirable for each of pacing pulses 82 to deliver approximately the same amount of energy to patient 26 or at least a minimum amount of energy. A minimum energy may be required in order to sufficiently capture heart 12. The amplitude of the pacing pulses 82 may not be a modifiable stimulation parameter value because energy storage module 62 may discharge at a predetermined rate. Accordingly, the pulse widths of pulses 82 may be modified in order to generate pulses having the desired energies. For example, pulses 82 having substantially equal energies or least energies above a minimum threshold required to capture heart 12 may be generated by increasing a pulse width of successive pacing pulses 82 to compensate for the decrease in amplitude resulting from the discharging of energy storage module 62. An energy of stimulation delivered to patient 26 via each pacing pulse 82 may generally be a function of the amplitude and pulse width of the respective pacing pulse 82.

As an example of how the pulse width of pacing pulses 82 may be modified to deliver pacing pulses 82 having substantially similar energies despite decreasing amplitudes, width 86B of pacing pulse 82B may be selected to be greater than width 86A of pacing pulse 82A. Because pacing pulse 82A has a greater amplitude than pacing pulse 82B, but pacing pulse 82A has a smaller pulse width than pacing pulse 82B, the energies of pacing pulses 82A, 82B may be substantially similar. As another example, width 86C of pacing pulse 82C may be greater than width 86B of pacing pulse 82B but less than a width 86D of pacing pulse 82D because the amplitude of pacing pulse 82C is less than the amplitude of pacing pulse 82B but greater than the amplitude of pacing pulse 82D. In this manner, the amplitude of each successive pacing pulse 82 may decrease as the pulse width of each successive pacing pulse increases. In the example shown in FIG. 5A, if the magnitude of the area under each of pacing pulses 82 is substantially constant, pacing pulses 82 may each deliver approximately the same amount of energy to patient 26.

Figure 5B:
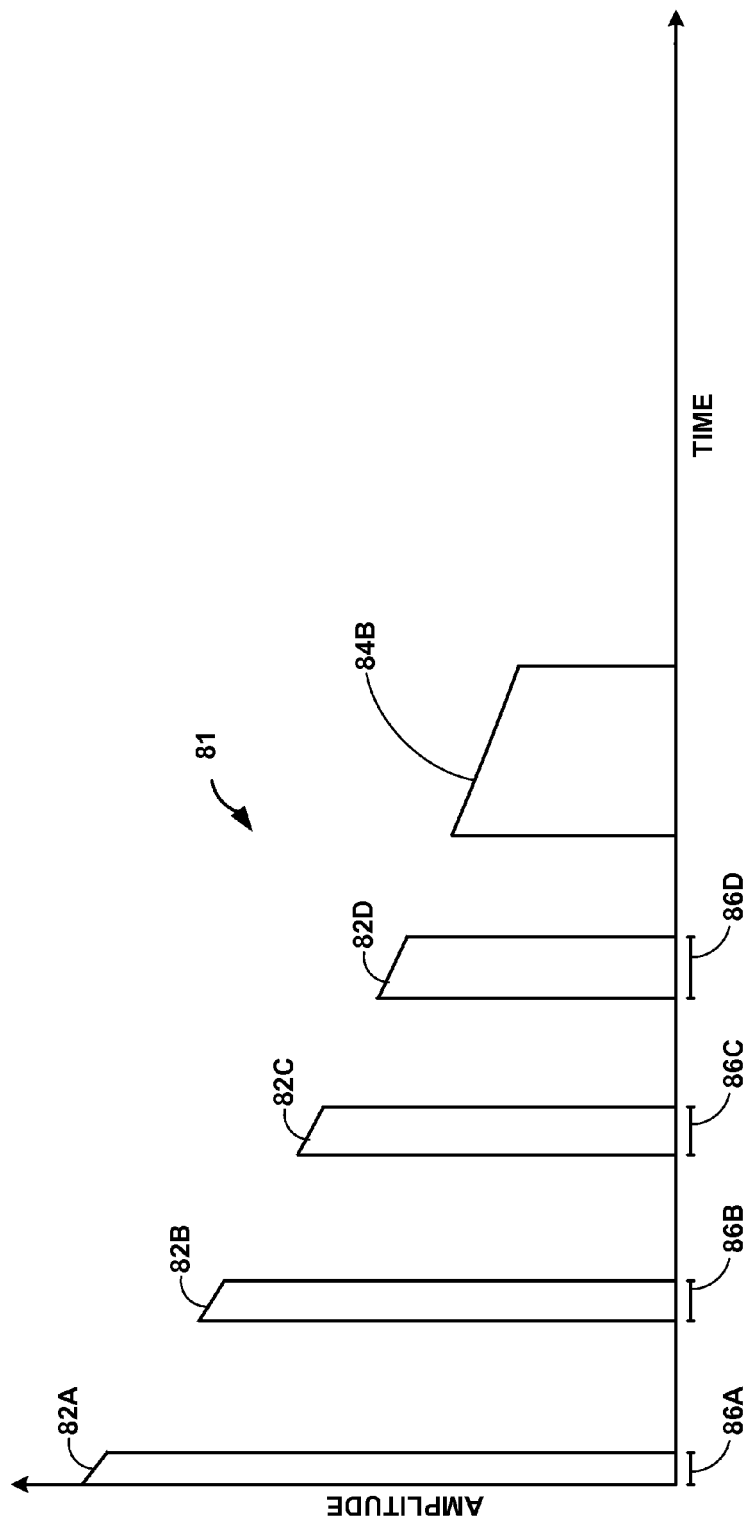
FIG. 5B is a conceptual illustration of a variation of the waveform of FIG. 5A, and illustrates a waveform including a monophasic truncated exponential shock pulse.

In the example illustrated in FIG. 5A, shock pulse 84A is a monophasic untruncated exponential shock pulse, e.g., shock pulse 84A has a single polarity and substantially completely decays exponentially. For example, shock pulse 84A may decay to an amplitude of approximately 0 volts. In contrast, waveform 81 of FIG. 5B is substantially similar to waveform 80 of FIG. 5A but includes a monophasic truncated exponential shock pulse 84B. Shock pulse 84B may be considered truncated, because it is terminated prior to complete exponential decay, e.g., prior to reaching an amplitude of approximately 0 volts. In other examples, a shock pulse that is delivered to induce an arrhythmia following the delivery of pacing pulses 82 may have any suitable waveform.

Although shock pulses 84A, 84B may have different waveforms, shock pulses 84A, 84B may each induce an arrhythmia in heart 12 of patient 26, e.g., a ventricular fibrillation, when delivered via extravascular electrodes 28 after a predetermined time period following pacing pulses 82. The ability of shock pulses 84A, 84B to induce an arrhythmia in heart 12 of patient 26 may be at least partially attributable to the timing of the shock pulses 84A, 84B. As previously described, in some examples, shock pulses 84A, 84B may be delivered during the vulnerable period of heart 12, which may be the time period following a paced cardiac event during which repolarization of the cardiac muscle of heart 12 is occurring, rendering heart 12 susceptible to induced fibrillation. The vulnerable period of heart 12 may generally correspond to the T-wave of the cardiac cycle.

Shock pulses 84A, 84B are each generated and delivered to patient 26 while energy storage module 62 discharges and without recharging of energy storage module 62 between the delivery of any of the pacing pulses 82 or between pacing pulses 82 and shock pulses 84A or 84B. That is, energy storage module 62 provides a common source of energy for pacing pulses 82 and shock pulses 84A or 84B. Sharing a common energy storage module 62 may enable external device 22 to induce an arrhythmia in patient 12 without the aid of separate energy storage modules for providing energy for pacing pulses 82 and for shock pulses 84A, 84B. In addition, sharing a common energy storage module 62 may enable external device 22 to induce an arrhythmia in patient 12 without the aid of IMD 24 (FIG. 2).

In some examples, separate energy storage modules may be used to generate pacing pulses 82 and shock pulses 84A, 84B. For example, if IMD 5 of FIG. 3B is used to induce an arrhythmia in heart 12, energy storage module 55A may provide the energy used to generate pacing pulses 82, while energy storage module 55B may provide the energy used to generate shock pulse 84A or 84B. In addition, energy storage module 55B may provide the energy used to generate defibrillation shocks.

Processor 50 of IMD 5 (FIG. 3B) may control stimulation generator 58 to charge energy storage module 55A and discharge energy storage module 55A to generate pacing pulses 82. Stimulation generator 58, under the control of processor 50, may then deliver the pacing pulses to patient 26 via electrodes electrically coupled to stimulation generator 58. In addition, processor 50 of IMD 5 may control stimulation generator 58 to charge energy storage module 55B and discharge energy storage module 55B to generate shock pulse 84A. Stimulation generator 58, under the control of processor 50, may then deliver shock pulse 84A to patient 26 via electrodes electrically coupled to stimulation generator 58. Energy storage modules 55A, 55B may be charged at different times or at the same time.

In general, the waveform diagrams shown in FIGS. 5A-7B are not necessarily drawn to any particular scale. As an example, S1-S1 intervals and S1-S2 intervals may be on the order of hundreds of milliseconds, while the pulse widths of pacing pulses 82 may be on the order of tens or hundreds of microseconds. Accordingly, the S1-S1 and S1-S2 intervals shown in FIG. 5A illustrate the general locations of the S1-S1 and S1-S2 intervals with respect to pacing pulses 82 and shock pulses 84 and are not necessarily drawn to any particular scale. The S1-S1 and S1-S2 intervals may be substantially larger than illustrated in FIG. 5A. For example, both the S1-S1 and S1-S2 intervals may be on the order of one thousand times larger than the widths 86 of pacing pulses 82.

Figure 6A:
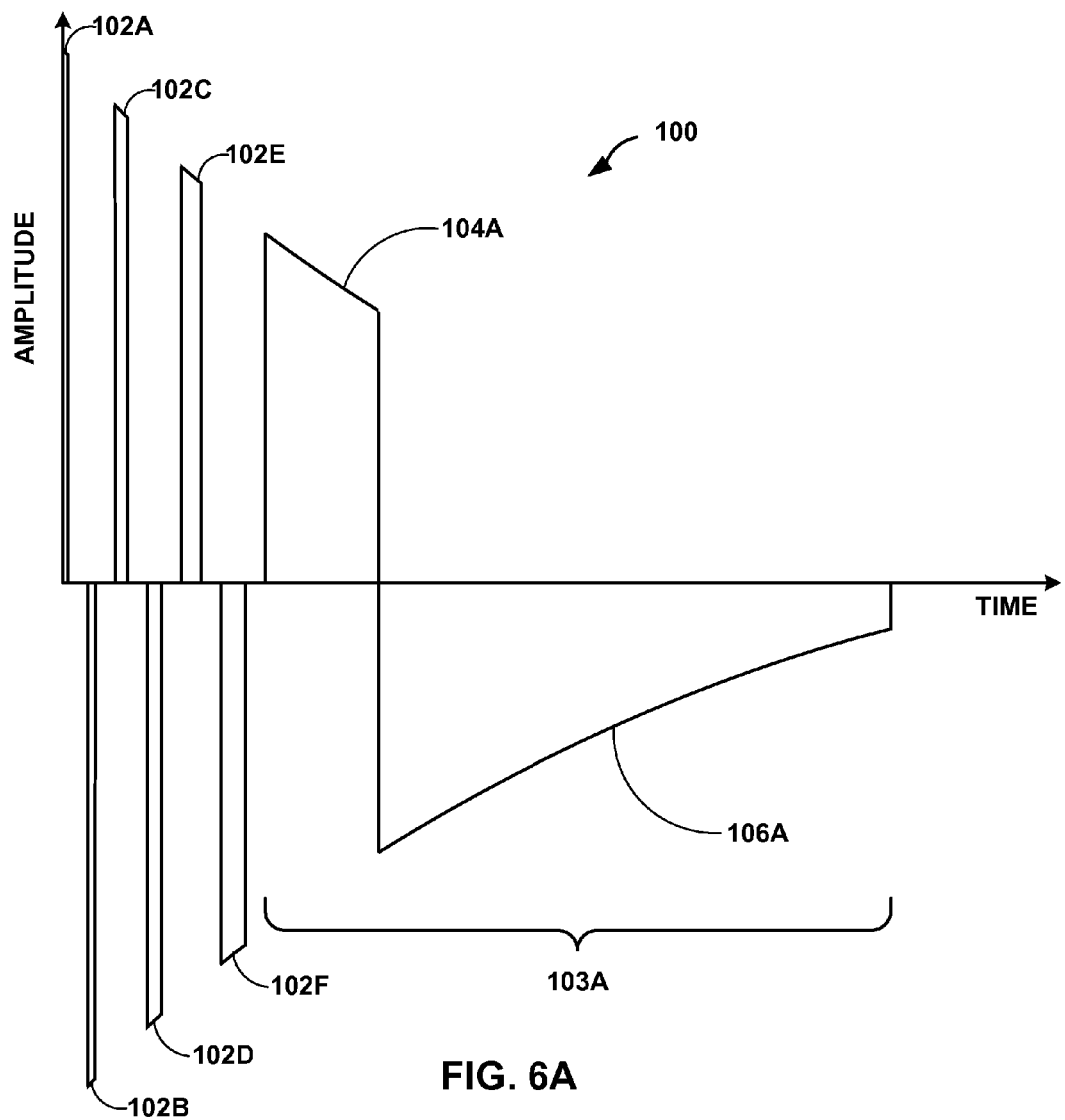
FIG. 6A is a conceptual illustration of another example waveform of electrical stimulation that a medical device may deliver to a patient via one or more extravascular electrodes to induce a cardiac arrhythmia.

FIG. 6A illustrates another example waveform 100 of electrical stimulation that external device 22 may deliver to patient 26 via extravascular electrodes 28 (FIG. 2) in order to induce an arrhythmia in heart 12 of patient 26. Waveform 100 includes a plurality of pacing pulses 102A-102F (collectively "pacing pulses 102") and shock pulse 103A. In the example shown in FIG. 6A, pacing pulses 102 and shock pulse 103A are generated with energy stored with energy storage module 62, e.g., without further charging of energy storage module 62 between the delivery of at least some of the pulses 102, 103A.

Processor 64 of external device 22 may control charging circuit 66 to charge energy storage module 62, from which the energy for pacing pulses 102 and shock pulse 103A may be obtained. In some examples, energy storage module 62 dissipates as pulses 102, 103A of waveform 100 are delivered to patient 12, such that once energy storage module 62 is charged, waveform 100 may be delivered to patient 12 without further charging of energy storage module 62. In other examples, energy storage module 62 may be charged between pacing pulses 102 or between the last pacing pulse 102F and shock pulse 103A.

In the example illustrated in FIG. 6A, consecutive pacing pulses 102 alternate in polarity, such that consecutive pacing pulses 102 generally have a biphasic waveform. For example, pacing pulses 102A, 102C, and 102E each have a positive polarity while pacing pulses 102B, 102D, and 102F each have a negative polarity. In other examples, all of pacing pulses 102 may have the same polarity or any other combination of positive and negative polarities. For example, pacing pulses 102 may have a waveform similar to that of pacing pulses 82 of FIG. 5A.

In all other regards, pacing pulses 102 may be substantially similar to pacing pulses 82 of FIGS. 5A and 5B. For example, the pulse width of each successive pacing pulse 102 may increase as the amplitude of each successive pacing pulse 102 decreases as a result of energy storage module 62 dissipating. Increasing the pulse width of each successive pacing pulse 102 may help maintain the amount of energy delivered to patient 26 by each pacing pulse 102 substantially constant. Additionally, processor 64 may initiate the delivery of pacing pulses 102 at constant time intervals (i.e., S1-S1 intervals) to achieve a substantially constant heart rate. In some cases, the S1-S1 interval between subsequent pacing pulses 102 may be less than the patient's intrinsic interval to increase the patient's heart rate above the patient's intrinsic heart rate and overdrive pace heart 12. Although the example illustrated in FIG. 6A includes six pacing pulses, other examples may include a fewer or greater number of pacing pulses.

After a predetermined time period has expired since the delivery of last pacing pulse 102F of waveform 100, processor 64 may initiate delivery of a shock pulse 103A, which is configured to induce an arrhythmia in heart 12 of patient 26. That is, shock pulse 103A has sufficient energy to induce an arrhythmia in heart 12 of patient 26 and is timed to increase the probability of inducing the arrhythmia. In the example illustrated in FIG. 6A, shock pulse 103A includes a biphasic truncated exponential shock pulse having positive and negative portions. Shock pulse 103A may be considered biphasic pulse because it includes a portion 104A with positive polarity and a portion 106A with a negative polarity. Shock pulse 103A may also be considered a truncated exponential pulse, because shock pulse 103A is terminated prior to complete exponential decay.

In other examples, separate energy storage modules, rather than a common energy storage module 62, may be used to generate pacing pulses 82 and shock pulses 84A, 84B. For example, if IMD 5 of FIG. 3B is used to induce an arrhythmia in heart 12, energy storage module 55A may provide the energy used to generate pacing pulses 102, while energy storage module 55B may provide the energy used to generate shock pulse 103A.

Figure 6B:
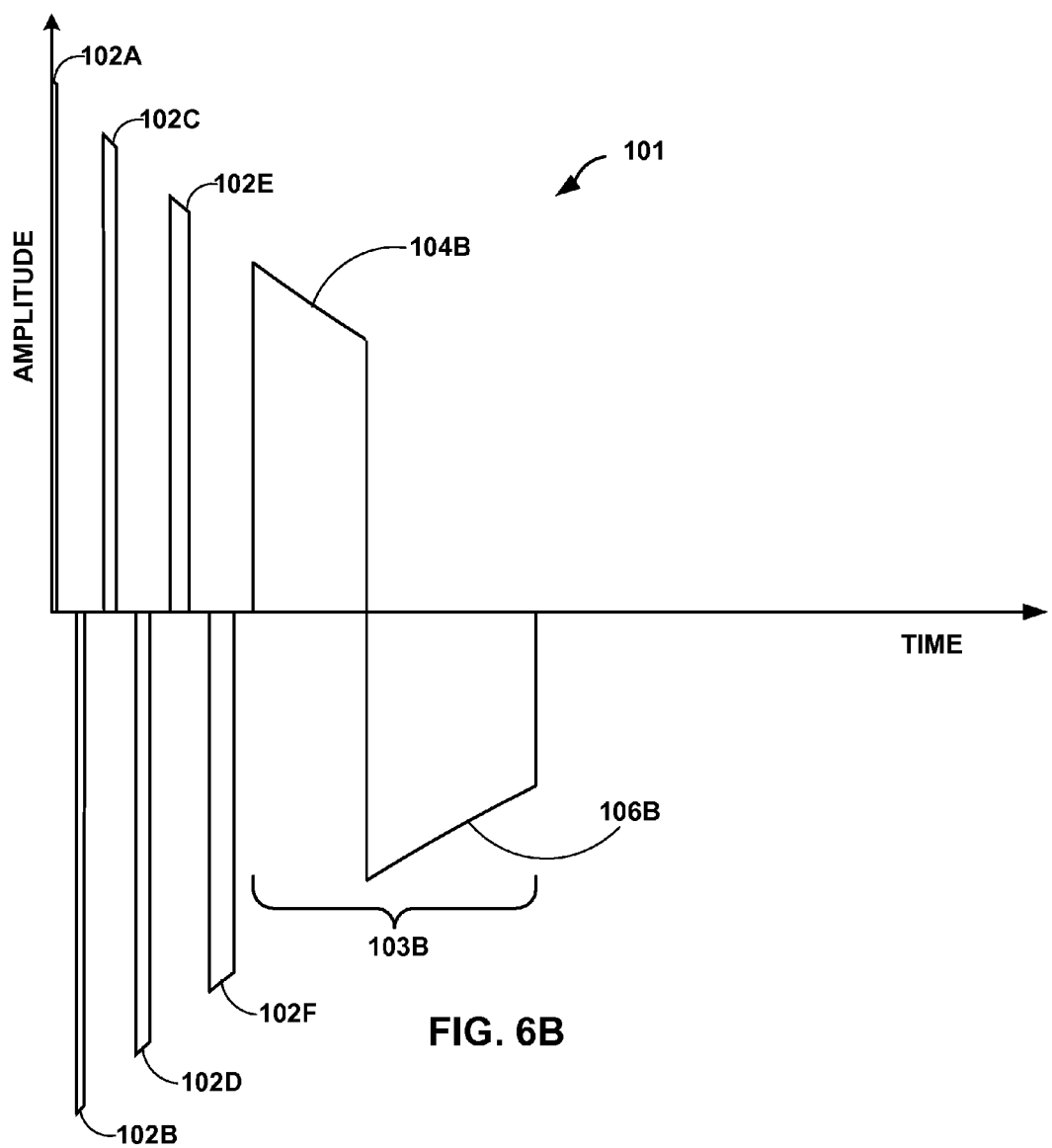
FIG. 6B is a conceptual illustration of a variation of the waveform of FIG. 6A, and illustrates a waveform including a symmetric biphasic exponential shock pulse.

Waveform 101 shown in FIG. 6B is substantially similar to waveform 100 of FIG. 6A, but includes a symmetric biphasic exponential shock pulse 103B rather than biphasic pulse 103A of waveform 100. Shock pulse 103B may be considered to have a symmetric biphasic waveform because approximately the same amount of energy is delivered by portion 104B with positive polarity and portion 106B with negative polarity. The magnitude of the amplitude of positive portion 104B may be less than the magnitude of the amplitude of negative portion 106B of shock pulse 103B because portion 106B of shock pulse 103B is delivered after shock pulse 104B, and, thus, is delivered when energy storage module 62 of external device 22 has a lower total stored energy level. Therefore, in order to deliver approximately the same amount of energy with positive portion 104B and negative portion 106B, negative portion 106B may have a longer duration, e.g., pulse width. Other types of symmetric pulses may include positive and negative portions having substantially equal pulse widths.

Figure 7A:
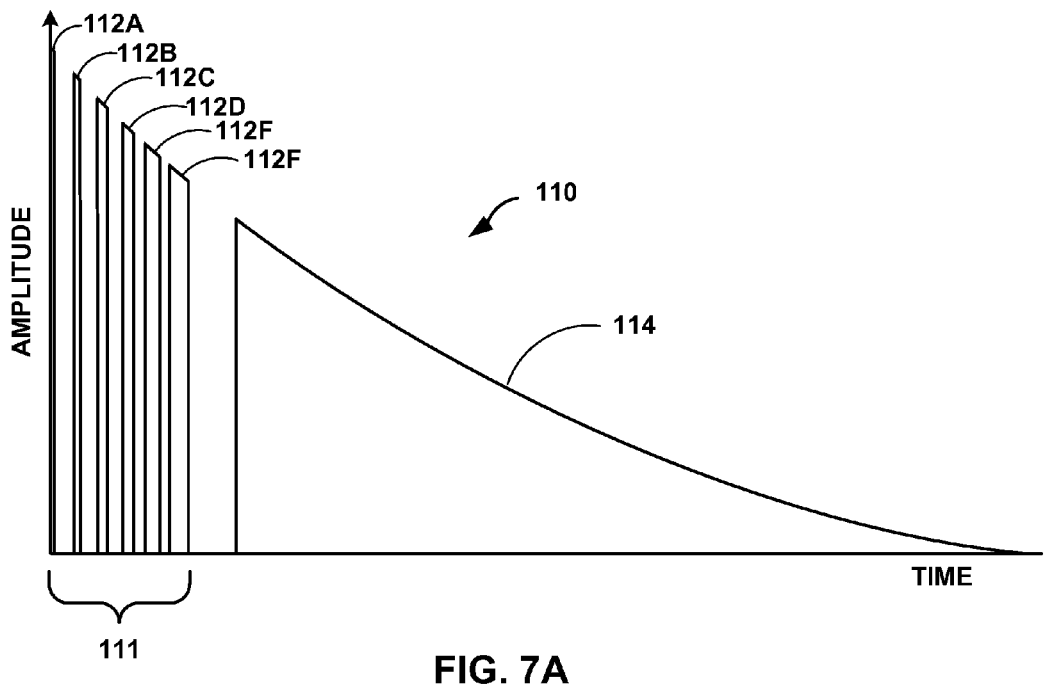
FIGS. 7A and 7B each illustrate example waveforms of electrical stimulation that a medical device may deliver to a patient via one or more extravascular electrodes to induce a cardiac arrhythmia.

FIG. 7A illustrates another example waveform 110 of electrical stimulation that external device 22 may use to induce an arrhythmia in heart 12 of patient 26. Waveform 110 includes a burst 111 of pulses 112A-112F (collectively "pulses 112"). Although the example of burst 111 illustrated in FIG. 7A includes six pulses, in other examples, burst 111 may include any number of pulses 112. Like pacing pulses 82 and 102 of FIGS. 5A, 5B, 6A, and 6B, in some examples, pulses 112 may be generated and delivered to patient 26 as energy storage module 62 discharges and without further charging of energy storage module 62. That is, in some examples, pulses 112 are generated with energy stored within energy storage module 62 of external device 22, e.g., without interim charging of energy storage module 62. Accordingly, energy storage module 62 dissipates as pulses 112 are delivered.

In some cases, it may be desirable to deliver pulses 112 having substantially similar energies. Thus, in some examples, waveform 110 may include pulses 112 that increase in pulse width as energy storage module 62 discharges in order to compensate for the decrease in voltage or current amplitude that results as energy storage module 62 discharges. In other examples, energy storage module 62 may be charged between the generation and delivery of at least some of the pulses 112.

In general, pulses 112 may have a pulse width of approximately 100 microseconds to approximately 20 milliseconds and a voltage amplitude of approximately 30 volts to approximately 800 volts or a current amplitude of approximately 0.1 amperes to approximately 10 amperes. Pulses 112 may be delivered at a frequency faster than the intrinsic cardiac cycle of heart 12 of patient 26. For example, processor 64 may control the delivery of pulses 112 at a rate that is faster than the patient's physiological maximum heart rate in order to cause irregular heart excitation and induce an arrhythmia (e.g., ventricular fibrillation). Delivering pulses 112 at a frequency faster than the patient's physiological maximum heart rate may causes various responses in various areas of heart 12. Some areas of heart 12 may recover from the electrical stimulation provided by pulses 112 better than others and maintain the heart's natural rhythm, while in other areas of heart 12, the delivery of pulses 112 may cause delayed excitation or premature excitation. The varying responses within heart 12 to the delivery of electrical stimulation via pulses 112 may induce an arrhythmia in heart 12.

The stimulation parameters of pulses 112, e.g., the pulse width, voltage or current amplitude, and frequency of pulses 112 in burst 111 may be selected to induce an arrhythmia in heart 12. In some examples, processor 64 may control delivery of pulses 112 via extravascular electrodes 28 at a frequency of approximately 10 Hertz (Hz) to approximately 250 Hz, such as approximately 12 Hz to approximately 50 Hz.

Additionally, in some examples, burst 111 comprising pulses 112 may be less than approximately 10 seconds in duration, and such as less than approximately 2 seconds in duration or approximately 0.1 seconds. As one example, processor 64 may control therapy interface 60 to deliver a sequence of approximately 25 Hz pulses 112 for a duration of approximately one second, e.g., such that the duration of burst 111 is approximately one second. Short burst durations, e.g., less than approximately 2 seconds, may be more tolerable to patient 26.

Delivery of a burst 111 of pulses 112 via extravascular electrodes may present additional considerations that are not encountered with intravascular electrodes. For example, the delivery of pulses 112 may induce tetanic skeletal muscle contractions when skeletal muscle is positioned between an electrode used to induce a cardiac arrhythmia and heart 12 of patient 12. Skeletal muscle contractions may incidentally result from the delivery of electrical stimulation when skeletal muscle is positioned between an extravascular electrode used to deliver the stimulation and the target stimulation site, e.g., heart 12. The skeletal muscle contractions may be cause discomfort or even perceptible pain to patient 26.

In some examples, when skeletal muscle is positioned between an electrode used to induce a cardiac arrhythmia (e.g., any of electrodes 28 of system 20 in FIG. 2, electrodes 10B, 11B of system 2B in FIG. 1B or electrodes 10C, 10D of system 2C in FIG. 1C) and heart 12, the frequency of pulses 112 may be configured to induce one continuous tetanic skeletal muscle contraction rather than a series of individual skeletal muscle contractions. By limiting the number of skeletal muscle contractions that may occur due to delivery of pulses 112 used to induce an arrhythmia in heart 12, perceptible pain patient discomfort resulting from skeletal muscle contractions may be minimized. Preventing the skeletal muscle of patient 26 from relaxing between pulses 112, i.e., inducing one continuous tetanic skeletal muscle contraction, may be preferred over allowing the skeletal muscle to relax between pulses and contract during pulse delivery. Therefore, the frequency of pulses 112 may be selected to help prevent skeletal muscle relaxation between consecutive pulses 112.

In the example illustrated in FIG. 7A, a shock pulse 114 is delivered after burst 111 of pulses 112. However, shock pulse 114 may not be necessary. In some cases, a cardiac arrhythmia may be induced simply by burst 111 of pulses 112. In examples in which shock pulse 114 is delivered to patient 26 via extravascular electrodes 28, processor 64 may deliver shock pulse 114 after a predetermined time period has elapsed since the delivery of the last pulse 112F of burst 111. For example, processor 64 may deliver shock pulse 114 after approximately five milliseconds to approximately two seconds has elapsed since delivery of the last pulse 112F of burst 111. In addition, although shock pulse 114 is illustrated as a monophasic untruncated exponential shock pulse, shock pulse 114 may take on any other suitable waveform. For example, shock pulse 114 may comprise a monophasic truncated exponential shock pulse (as described with respect to FIG. 5B), a biphasic truncated exponential shock pulse (a described with respect to FIG. 6A), or a symmetric biphasic shock pulse (as described with respect to FIG. 6B).

In some examples, separate energy storage modules may be used to generate pulses 112. For example, if IMD 5 of FIG. 3B is used to induce an arrhythmia in heart 12, energy storage module 55A may provide the energy used to generate some of the pulses 112, while energy storage module 55B may provide the energy used to other pulses 112.

Figure 7B:
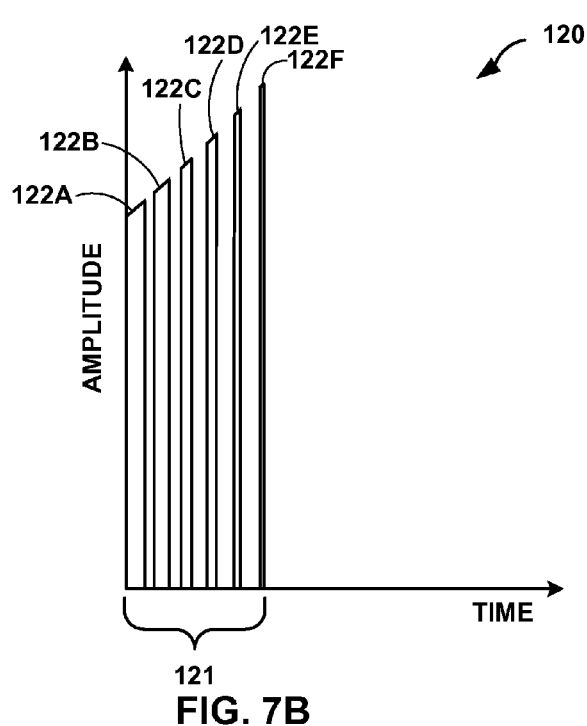

FIG. 7B illustrates yet another example waveform 120 of electrical stimulation that external device 22 may deliver to patient 26 via extravascular electrodes in order to induce an arrhythmia in heart 12. Waveform 120 includes a burst 121 of pulses 122. Burst 121 and pulses 122 may be substantially similar to burst 111 and pulses 112 of FIG. 7A. However, in contrast to the waveforms previously described, successive pulses 122 increase in amplitude. Bursts 121 may be delivered as energy storage module 62 is charging. Although energy is discharged from energy storage module 62 to deliver each burst, successive pulses 122 increase in amplitude as energy storage module 62 charges. As pulses 122 of burst 121 increase in amplitude, the pulse width of consecutive pulses 122 may decrease in order to help deliver pulses 122 having substantially equal energies.

Although the delivery of burst 121 of pulses 122 while energy storage module 62 is charging is described with respect to a burst of pulses 121, processor 64 may also deliver pacing and/or shock pulses while energy storage module 62 is charging. Accordingly, in some examples, consecutive pacing pulses may have increasing amplitudes and/or a shock pulse delivered after one or more pacing pulses may have a greater amplitude than the prior delivered pacing pulses of the electrical stimulation waveform. In such examples, the pulse widths of the pacing pulses may be modified in order to maintain pacing pulses having substantially constant energies.

As with pulses 112 of burst 111 of FIG. 7A, pulses 122 of burst 121 may be delivered at a frequency faster than the patient's physiological maximum heart rate to induce a cardiac arrhythmia. The frequency of pulses 122 may also be selected to induce one continuous tetanic skeletal muscle contraction throughout the duration of burst 121. Additionally, although a shock pulse is not illustrated in the example of FIG. 7B, processor 64 may deliver a shock pulse to heart 12 of patient 26 after a predetermined time period has elapsed since the delivery of the last pulse 122 of burst 121.

FIGS. 5A-7B illustrate various pulse waveforms for purposes of example. However, pacing pulses 82 and 102, shock pulses 84, 103, and 114, and pulses 112 and 122 of bursts 111 and 121 are not limited to their illustrated waveforms. Any type of stimulation pulse described herein, e.g., pacing, shock, and bursts of pulses, may be monophasic or multiphasic, e.g., biphasic. Additionally, when one or more pacing, shock, or burst pulses are monophasic, each pulse may have either a positive or a negative polarity.

Figure 8:
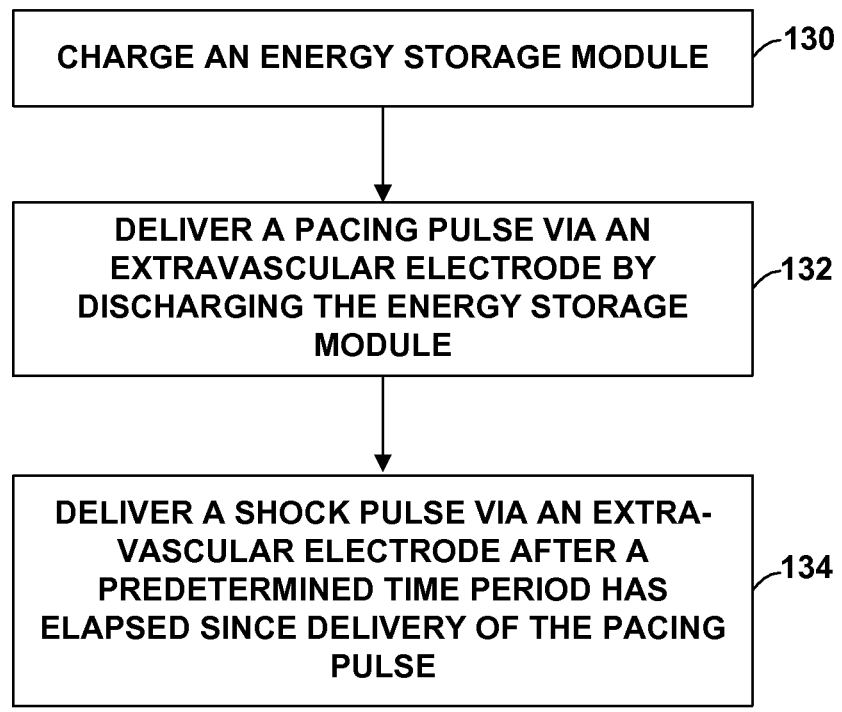
FIG. 8 is a flow diagram illustrating one example technique for inducing a cardiac arrhythmia via extravascular electrodes.

FIG. 8 is a flow diagram illustrating an example technique for inducing a cardiac arrhythmia by delivering electrical stimulation to a patient via extravascular electrodes. Although, the technique shown in FIG. 8 is generally described with respect to external device 22 including processor 64, the disclosure is not so limited. In other examples, any medical device capable of extravascularly stimulating a patient's heart may be used to induce a cardiac arrhythmia, such as IMD 4 of FIGS. 1A-1C.

Processor 64 may control charging circuit 66 of external device 22 to charge energy storage module 62 to a voltage (or current) level sufficient to deliver one or more stimulation pulses configured to induce an arrhythmia in the patient (130). Processor 64 may control therapy interface 60 to deliver one or more pacing pulses to excite heart 12 (132). For example, processor 64 may activate the switches of therapy interface 60 to electrically connect energy storage module 64 to electrodes 28, and thereby deliver one or more pacing pulses to heart 12 by discharging energy storage module 62.

In some examples, processor 64 may control therapy interface 60 to deliver a plurality of pacing pulses (e.g., pacing pulses 82 of FIGS. 5A and 5B) at a constant time interval in order to control the rate at which heart 12 beats. The time interval between subsequent pacing pulses (i.e., the S1-S1 interval) may be shorter that the heart's intrinsic interval, which may cause heart 12 to beat at a heart rate faster than its intrinsic rate. As one example, processor 64 may deliver approximately four to approximately eight pacing pulses to heart 12.

After a predetermined time period has passed since the delivery of the last pacing pulse, processor 64 may control therapy interface 60 to initiate delivery of a shock pulse configured to induce an arrhythmia (134). For example, processor 64 may activate the switches of therapy interface 60 to electrically connect energy storage module 62 to electrodes 28, and thereby deliver the shock pulse to heart 12 by further discharging energy storage module 62. In this way, the energy for generating the pacing and shock pulses may be provided by a common energy source, i.e., energy storage module 62.

The predetermined time period that separates the deliver of the last pacing pulse and the delivery of the shock pulse (e.g., the S1-S2 interval) may be selected to synchronize the shock pulse with the vulnerable period of the cardiac cycle of patient 26. As previously described, the vulnerable period of the cardiac cycle may generally correspond to the T-wave of a cardiac cycle. When the patient's heart rate is substantially constant, the timing of the vulnerability period, e.g., T-wave of the ECG signal, may also be substantially constant. Pacing the patient's heart rate above the patient's intrinsic heart rate may also increase the consistency and predictability of the vulnerable period timing. In this manner, the delivery of the pacing pulses may aid in synchronizing the shock pulse with the vulnerable period of the cardiac cycle and, therefore, increase the likelihood of inducing arrhythmia with the shock pulse.

After the delivery of the shock pulse (134) to patient 26 via the extravascular electrode, an arrhythmia may be observed. In some cases, a clinician may deliver one or more defibrillation shocks to patient 26 via the extravascular electrodes or via intravascular electrodes, e.g., as part of DFT testing. For example, defibrillation may be first attempted using IMD 24. If defibrillation is unsuccessful using IMD 24, processor 64 may control energy storage module 62 to deliver one or more defibrillation shocks to patient 26.

Figure 9:
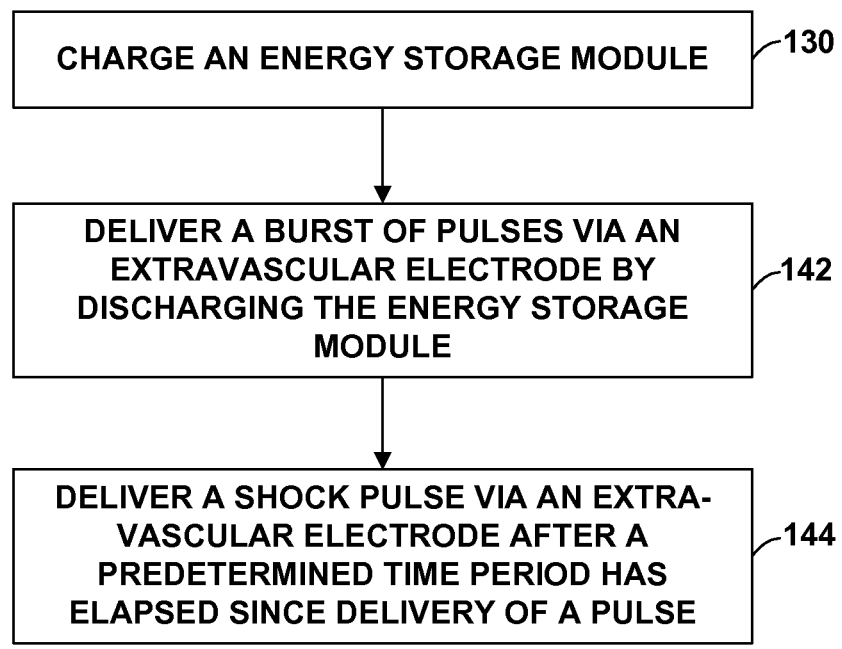
FIG. 9 is a flow diagram illustrating another example technique for inducing a cardiac arrhythmia via extravascular electrodes.

FIG. 9 is a flow diagram illustrating another example technique that may be employed in order to induce a cardiac arrhythmia by delivering of electrical stimulation to patient 26 via one or more extravascular electrodes. Although, the technique shown in FIG. 8 is generally described with respect to external device 22 including processor 64, the disclosure is not so limited. In other examples, any medical device capable of extravascularly stimulating a patient's heart may be used to induce a cardiac arrhythmia, such as IMD 4 of FIGS. 1A-1C.

Processor 64 of external device may control charging circuit 66 to charge energy storage module 62 to a voltage level sufficient to deliver one or more stimulation pulses configured to induce an arrhythmia in the patient (130). Processor 64 may control therapy interface 60 to deliver a burst of pulses to heart 12 (142). For example, processor 64 may activate the switches of stimulation generator 58 to electrically connect energy storage module 62 to electrodes 28 (FIG. 2), and generate and deliver a burst of pulses to heart 12 as energy storage module 62 discharges. Energy storage module 62 may discharge as therapy interface 60 draws the energy required to generate the burst of pulses from energy storage module 62.

In some examples, the pulses within the burst of pulses may be delivered at a frequency faster than the cardiac cycle of heart 12 of patient 26. For example, as described with respect to FIGS. 7A and 7B, the pulses may be delivered at a rate faster than the patient's physiological maximum heart rate. Delivering the pulses at a frequency faster than the patient's physiological maximum heart rate may induce an arrhythmia in heart 12. In some examples, after a predetermined time period has expired since the delivery of the last pacing pulse of the burst of pulses, processor 64 may initiate delivery of a shock pulse configured to induce an arrhythmia (144). For example, processor 64 may activate the switches of therapy interface 60 to electrically connect energy storage module 62 to electrodes 28, and generate and deliver the shock pulse to heart 12 by further discharging energy storage module 62. Energy storage module 62 may discharge as therapy interface 60 draws the energy required to generate the burst of pulses and the shock pulse from energy storage module 62.

In some cases, the delivery of the burst of pulses (142) may be sufficient to induce a cardiac arrhythmia, and delivery of the shock pulse (144) may not be necessary. Accordingly, in some examples, the technique shown in FIG. 9 may not require the delivery of a shock pulse to patient 26 via one or more extravascular electrodes.

After the delivery of the shock pulse (144) or after the delivery of the burst of pulses (142) to patient 26 via the extravascular electrode, an arrhythmia may be observed. In some cases, a clinician may deliver one or more defibrillation shocks to patient 26 via the extravascular electrodes or via intravascular electrodes, e.g., as part of DFT testing. For example, defibrillation may be first attempted using IMD 24. If defibrillation is unsuccessful using IMD 24, processor 64 may control energy storage module 62 to deliver one or more defibrillation shocks to patient 26.

In general, the pacing pulses and the shock pulses described herein may have any suitable waveform shape, and are not limited to the specific combinations described herein. The techniques described in this disclosure, including those attributed to IMD 4, external device 22, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable data storage medium such as RAM, ROM, NVRAM, EEPROM, FLASH memory, magnetic data storage media, optical data storage media, or the like. The instructions may be executed to support one or more aspects of the functionality described in this disclosure.

In other examples, the techniques described as being performed by processor 50 of IMD 4 or processor 64 of external device 22 may be performed in whole or in part by a processor of another device, such as a medical device programmer. In addition, the therapy modules (e.g., stimulation generator 58 of IMD 4 or therapy interface 60 of external device 22), charging of an energy storage module, and/or the energy storage modules described herein may be located in another device, such as a medical device programmer, which may facilitate the generation and delivery of a sequence of pulses to induce a cardiac arrhythmia in a patient, as described herein.

Various examples of have been described in this disclosure. These and other examples are within the scope of the following claims.

The invention claimed is:

1. A method comprising:
generating a burst of pulses comprising a plurality of pulses from energy stored within an energy storage module; and
delivering the burst of pulses via an extravascular electrode to a heart of a patient, wherein the burst of pulses is configured to induce an arrhythmia in a heart of a patient, and wherein each of the pulses of the burst of pulses comprises a respective pulse width and the pulse widths of the pulses increase with each successive pulse of the burst of pulses.

2. The method of claim 1, further comprising charging the energy storage module prior to delivering the burst of pulses to provide the energy stored within the energy storage module.

3. The method of claim 1, further comprising charging the energy storage module while delivering the burst of pulses to provide the energy stored within the energy storage module.

4. The method of claim 1, further comprising delivering a shock pulse to the heart of the patient via the extravascular electrode after a predetermined time period has elapsed since the delivery of a last pulse of the burst of pulses.

5. The method of claim 4, wherein the predetermined period of time is approximately 240 milliseconds and approximately 400 milliseconds.

6. The method of claim 4, wherein a waveform of the shock pulse comprises at least one of a monophasic untruncated exponential waveform, a monophasic truncated exponential waveform, a biphasic truncated exponential waveform or a symmetric biphasic waveform.

7. The method of claim 1, wherein each of the pulses of the burst of pulses comprises a respective amplitude and the amplitudes of the pulses decrease with each successive pulse of the burst of pulses.

8. The method of claim 1, wherein the extravascular electrode comprises at least one of an extrathoracic electrode, a subcutaneous electrode, a submuscular electrode, an epicardial electrode or an intramural electrode.

9. The method of claim 1, wherein delivering the burst of pulses to the heart of the patient via the extravascular electrode comprises delivering the pulses at a frequency of approximately 10 Hertz to approximately 250 Hertz.

10. The method of claim 1, wherein each pulse of the plurality of pulses comprises at least one of a voltage amplitude of approximately 300 Volts to approximately 800 Volts or a pulse width of approximately 0.1 milliseconds to approximately 2 milliseconds.

11. The method of claim 1, wherein the burst of pulses has a duration of approximately 0.1 seconds to approximately 2 seconds.

12. The method of claim 1, further comprising delivering a defibrillation shock to the heart of the patient to terminate the arrhythmia.

13. The method of claim 12, further comprising discharging the energy storage module to generate the defibrillation shock.

14. The method of claim 13, further comprising, prior to discharging the energy storage module to generate the defibrillation shock, charging the energy storage module.

15. A system comprising:
an extravascular electrode;
a therapy module comprising an energy storage module; and
a processor that controls the therapy module to deliver a burst of pulses comprising a plurality of pulses to a patient via the extravascular electrode, wherein the burst of pulses is configured to induce an arrhythmia in the heart of the patient, wherein each of the pulses of the burst of pulses comprises a respective pulse width and the pulse widths of the pulses increase with each successive pulse of the burst of pulses, and wherein the energy storage module discharges to provide energy to the therapy module to generate the plurality of pulses.

16. The system of claim 15, wherein the processor controls the therapy module to deliver the plurality of pulses of the burst of pulses at a frequency of approximately 10 Hertz to approximately 250 Hertz.

17. The system of claim 15, wherein each of the pulses of the plurality of pulses comprises at least one of a voltage amplitude of approximately 300 Volts to approximately 800 Volts or a pulse width of approximately 0.1 milliseconds to approximately 2 milliseconds.

18. The system of claim 15, wherein the burst of pulses has a duration of approximately 0.1 seconds to approximately 2 seconds.

19. The system of claim 15, wherein the processor controls the therapy module to deliver a shock pulse to the heart of the patient after a predetermined time period has elapsed since the delivery of a last pulse of the burst of pulses.

20. The system of claim 19, wherein the predetermined period of time is approximately 0.005 seconds to about 2 seconds.

21. The system of claim 19, wherein the energy storage module discharges to provide energy to the therapy module to generate the burst of pulses and further discharges without interim charging to provide energy to the therapy module to generate the shock pulse.

22. The system of claim 19, wherein a waveform of the shock pulse comprises at least one of a monophasic untruncated exponential, monophasic truncated exponential, biphasic truncated exponential, or symmetric biphasic.

23. The system of claim 15, wherein each of the pulses of the burst of pulses comprises a respective amplitude and the amplitudes of the pulses decrease with each successive pulse of the burst of pulses.

24. The system of claim 15, wherein the extravascular electrode comprises at least one of an extrathoracic electrode, a subcutaneous electrode, a submuscular electrode, an epicardial electrode or an intramural electrode.

25. The system of claim 15, wherein the energy storage module comprises an energy storage module of at least one of an implantable cardiac device, an external defibrillator, or an external programmer.

26. The system of claim 15, wherein the processor controls the therapy module to discharge the energy storage module to generate a defibrillation shock and deliver the defibrillation shock to the patient.

27. The system of claim 19, wherein the processor controls the therapy module to charge the energy storage module prior to generating the defibrillation shock.

28. A system comprising:
means for generating a burst of pulses comprising a plurality of pulses from energy stored within an energy storage module; and
means for delivering the burst of pulses via an extravascular electrode to a heart of a patient, wherein the burst of pulses is configured to induce an arrhythmia in a heart of a patient, and wherein each of the pulses of the burst of pulses comprises a respective pulse width and the pulse widths of the pulses increase with each successive pulse of the burst of pulses.

29. The system of claim 28, further comprises means for delivering a shock pulse to the heart of the patient via the extravascular electrode after a predetermined time period has elapsed since the delivery of a last pulse of the burst of pulses.

\* \* \* \* \*